United States Patent
Archdeacon

(10) Patent No.: US 11,684,270 B2
(45) Date of Patent: *Jun. 27, 2023

(54) METHOD FOR COLLECTION OF BLOOD PRESSURE MEASUREMENT

(71) Applicant: Bodymatter, Inc., Newport Beach, CA (US)

(72) Inventor: Ryan Patrick Archdeacon, Newport Beach, CA (US)

(73) Assignee: Bodymatter, Inc., Newport Beach, CA (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/020,756

(22) Filed: Sep. 14, 2020

(65) Prior Publication Data

US 2020/0405159 A1   Dec. 31, 2020

Related U.S. Application Data

(63) Continuation of application No. 14/550,816, filed on Nov. 21, 2014, now Pat. No. 10,786,161.
(Continued)

(51) Int. Cl.
*A61B 5/021* (2006.01)
*A61B 5/0205* (2006.01)
(Continued)

(52) U.S. Cl.
CPC ............. *A61B 5/0205* (2013.01); *A61B 5/25* (2021.01); *A61B 5/6801* (2013.01);
(Continued)

(58) Field of Classification Search
None
See application file for complete search history.

(56) References Cited

U.S. PATENT DOCUMENTS

| 7,179,228 B2 | 2/2007 | Banet |
| 7,539,532 B2 | 5/2009 | Tran |

(Continued)

FOREIGN PATENT DOCUMENTS

| WO | 2012092303 A1 | 7/2012 |
| WO | 2014022906 A1 | 2/2014 |
| WO | 2014089665 A1 | 6/2014 |

OTHER PUBLICATIONS

"High Blood Pressure", MedlinePlus, Retrieved from: https://medlineplus.gov/highbloodpressure.html, Topic last reviewed Apr. 19, 2018, Last updated Nov. 2019, 9 pgs.
(Continued)

*Primary Examiner* — Etsub D Berhanu
(74) *Attorney, Agent, or Firm* — KPPB LLP

(57) ABSTRACT

A system to measure blood pressure of a person comprises a software that is configured to obtain two or more sensor information from one or more sensor near simultaneously. The sensor information comprises data points, from which at least one data feature can be derived. Based on the data features derived from the data points, a value of the cardiovascular time delay can be derived. The system can further derive a blood pressure value based on the cardiovascular time delay, and provide the value of the blood pressure, the cardiovascular delay, or other metrics derived from the cardiovascular delay to a user. The sensors can be placed in one or more mobile or wearable devices, which can communicate with each other wirelessly.

28 Claims, 12 Drawing Sheets

Related U.S. Application Data

(60) Provisional application No. 61/948,947, filed on Mar. 6, 2014, provisional application No. 61/914,335, filed on Dec. 10, 2013, provisional application No. 61/909,661, filed on Nov. 27, 2013.

(51) Int. Cl.
    *A61B 5/00*          (2006.01)
    *A61B 5/25*          (2021.01)
    *A61B 5/02*          (2006.01)
    *A61B 5/024*        (2006.01)

(52) U.S. Cl.
    CPC .......... *A61B 5/6898* (2013.01); *A61B 5/7278* (2013.01); *A61B 5/021* (2013.01); *A61B 5/02007* (2013.01); *A61B 5/02416* (2013.01)

(56) References Cited

U.S. PATENT DOCUMENTS

| | | |
|---|---|---|
| 7,674,231 B2 | 3/2010 | McCombie et al. |
| 8,313,439 B2 | 11/2012 | McCombie et al. |
| 8,579,827 B1 | 11/2013 | Rulkov et al. |
| 8,672,854 B2 | 3/2014 | McCombie et al. |
| 8,790,264 B2 | 7/2014 | Sandler et al. |
| 8,821,415 B2 | 9/2014 | Al-Ali et al. |
| 10,786,161 B1 | 9/2020 | Archdeacon |
| 2001/0003792 A1 | 6/2001 | Ogura et al. |
| 2001/0008953 A1 | 7/2001 | Honda et al. |
| 2002/0058876 A1 | 5/2002 | Chen et al. |
| 2004/0117212 A1 | 6/2004 | Kong et al. |
| 2005/0228299 A1 | 10/2005 | Banet |
| 2005/0228300 A1 | 10/2005 | Jaime et al. |
| 2006/0211942 A1 | 9/2006 | Hoctor et al. |
| 2007/0066898 A1 | 3/2007 | Hendriks et al. |
| 2007/0276196 A1 | 11/2007 | Donaldson et al. |
| 2008/0082004 A1 | 4/2008 | Banet et al. |
| 2008/0249382 A1 | 10/2008 | Oh et al. |
| 2009/0030292 A1 | 1/2009 | Bartnik et al. |
| 2009/0157429 A1 | 6/2009 | Lee et al. |
| 2009/0203998 A1 | 8/2009 | Klinghult et al. |
| 2009/0216132 A1 | 8/2009 | Orbach |
| 2010/0160794 A1 | 6/2010 | Banet et al. |
| 2010/0179438 A1 | 7/2010 | Heneghan et al. |
| 2010/0268094 A1 | 10/2010 | Hasling et al. |
| 2010/0280396 A1 | 11/2010 | Zhang |
| 2011/0009714 A1 | 1/2011 | Zong |
| 2011/0288421 A1 | 11/2011 | Banet et al. |
| 2012/0071774 A1 | 3/2012 | Osorio et al. |
| 2012/0203077 A1 | 8/2012 | He et al. |
| 2013/0072145 A1 | 3/2013 | Dantu |
| 2013/0109989 A1 | 5/2013 | Busse et al. |
| 2013/0178736 A1 | 7/2013 | Pahlevan et al. |
| 2013/0338460 A1 | 12/2013 | He et al. |
| 2014/0249443 A1 | 9/2014 | Banet et al. |
| 2015/0112606 A1 | 4/2015 | He et al. |
| 2015/0164351 A1 | 6/2015 | He et al. |

OTHER PUBLICATIONS

Arza et al., "Pulse Transit Time and Pulse Width as Potential Measure for Estimating Beat-to-Beat Systolic and Diastolic Blood Pressure", Computing in Cardiology Conference (CinC), 2013, pp. 887-890.

Asmar et al., "Assessment of Arterial Distensibility by Automatic Pulse Wave Velocity Measurement", Hypertension. 1995; 26: 485-490.

Bera, "Bioelectrical Impedance Methods for Noninvasive Health Monitoring: A Review", Hindawi Publishing Corporation, Journal of Medical Engineering, vol. 2014, Article ID 381251, 28 pages.

Blacher et al., "Aortic Pulse Wave Velocity as a Marker of Cardiovascular Risk in Hypertensive Patients", American Heart Association, 1999;33:1111-1117.

Chandrasekaran, "Measuring Vital Signs Using Smart Phones", Master of Science Thesis for University of North Texas, pp. 1-146, Dec. 2010.

Chandrasekaran et al., "Cuffless Differential Blood Pressure Estimation Using Smart Phones", IEEE Transactions on Biomedical Engineering, Apr. 2013, vol. 60, No. 4, pp. 1080-1089.

Chen et al., "A New Methodology of Continuous and Noninvasive Blood Pressure Measurement by Pulse Wave Velocity", Automation, Robotics and Vision, pp. 1018-1023, Dec. 7-10, 2010.

Chen et al., "Continuous and Noninvasive Blood Pressure Measurement: A Novel Modeling Methodology of the Relationship Between Blood Pressure and Pulse Wave Velocity", Annals of Biomedical Engineering, vol. 37, No. 11, Nov. 2009, pp. 2222-2233.

Chen et al., "The Relationship between Different Pulse Wave Velocity and Systolic/Diastolic Pressure", Industrial Electronics and Applications, 2008, pp. 1185-1190.

Gesche et al., "Continuous blood pressure measurement by using the pulse transit lime: comparison to a cuff-based method", Eur J Appl Physiol, Published May 10, 2011.

Gubner et al., "Ballistocardiography: An Appraisal of Technic, Physiologic Principles, and Clinical Value", American Heart Association, 1953;7:268-286.

Hansen et al., "Prognostic Value of Aortic Pulse Wave Velocity as Index of Arterial Stiffness in the General Population", American Heart Association, 2006;113:664-670.

Laurent et al., "Aortic Stiffness is an Independent Predictor of All-Cause and Cardiovascular Mortality in Hypertensive Patients", American Heart Association, 2001 ;37:1236-1241.

Llango et al., "A Non-Invasive Blood Pressure Measurement using Android Smart Phones", IOSR Journal of Dental and Medical Sciences (IOSR-JDMS), Jan. 2014, vol. 13, Issue 1 Ver. IV, pp. 28-31.

Meaume et al., "Aortic Pulse Wave Velocity Predicts Cardiovascular Mortality in Subjects >70 Years of Age", American Heart Association, 2001 ;21:2046-2050.

Nyboer et al., "Electrical Impedance Plethysmography: A Physical and Physiologic Approach to Peripheral Vascular Study", American Heart Association, 1950;2:811-821.

O'Rourke et al., "Clinical Applications of Arterial Stiffness; Definitions and Reference Values", American Journal of Hypertension, Ltd., May 2002—vol. 15, No. 5.

Payne et al., "Pulse transit lime measured from the ECG: an unreliable marker of beat-to-beat blood pressure", Journal of Applied Physiology, 2006 First Published Sep. 1, 2005, 100: pp. 136-141.

Reusz et al., "Reference Values of Pulse Wave Velocity in Healthy Children and Teenagers", American Heart Association, 2010;56:217-224.

Roche, "Transmitting Biological Waveforms Using a Cellular Phone", Master of Science Thesis for University of Pittsburgh School of Engineering, Dec. 2, 2004.

Shin et al., "Non-constrained monitoring of systolic blood pressure on a weighing scale", Physiological Measurement 30 (2009) 679-693.

Stankus, "Comparison of Point-to-Point and Multipoint Human Artery Pulse Wave Transit Time Measurement Algorithms", Department of Informatics Engineering, Klaipeda University 2012 No. 7 (123).

Tannenbaum et al., "Relationship between Ballistocardiographic Forces and Certain Events in the Cardiac Cycle", American Heart Association, 1952;6:586-592.

Tyrrell et al., "Elevated Aortic Pulse Wave Velocity, a Marker of Arterial Stiffness, Predicts Cardiovascular Events in Well-Functioning Older Adults", American Heart Association, 2005; 111:3384-3390.

Verma et al., "AudioDAQ: Turning the Mobile Phone's Ubiquitous Headset Port into a Universal Data Acquisition 6 Interface", Proceeding SenSys '12 Proceedings of the 10th ACM Conference on Embedded Network Sensor Systems, 2012, pp. 197-210.

Vlachopoulos et al., "Prediction of Cardiovascular Events and All-Cause Mortality With Arterial Stiffness", Journal o the American College of Cardiology, vol. 55, No. 13, 2010.

(56) References Cited

OTHER PUBLICATIONS

Wong et al., "An Evaluation of the Cuffless Blood Pressure Estimation Based on Pulse Transit Time Technique: a Half Year Study on Normotensive Subjects", Springer Science+ Business Media, LLC, Apr. 18, 2009.

Visvanathan et al., "Estimation of Blood Pressure Levels from Reflective Photoplethysmograph using Smart Phones", Innovation Labs, Tala Consultancy Services Ltd., India, Downloaded on Oct. 10, 2014.

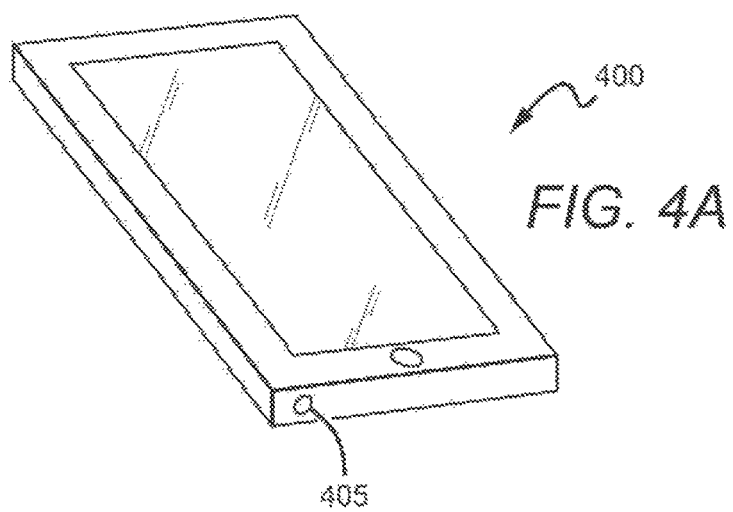
FIG. 4A
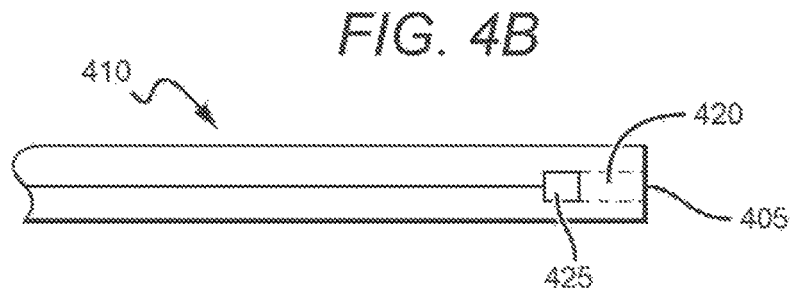
FIG. 4B
FIG. 4C
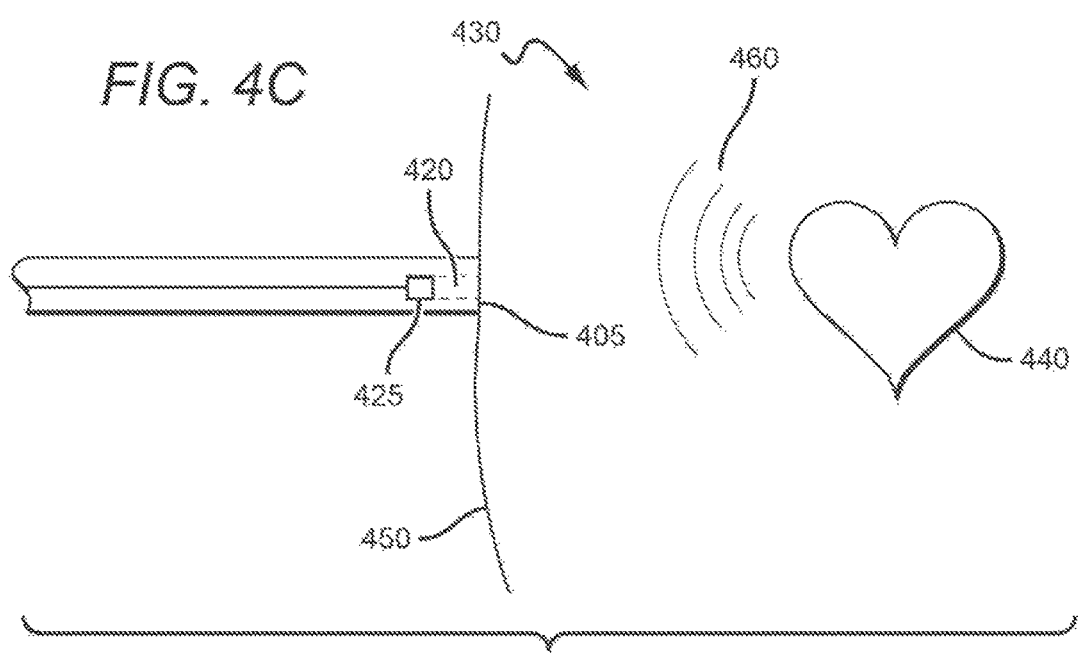

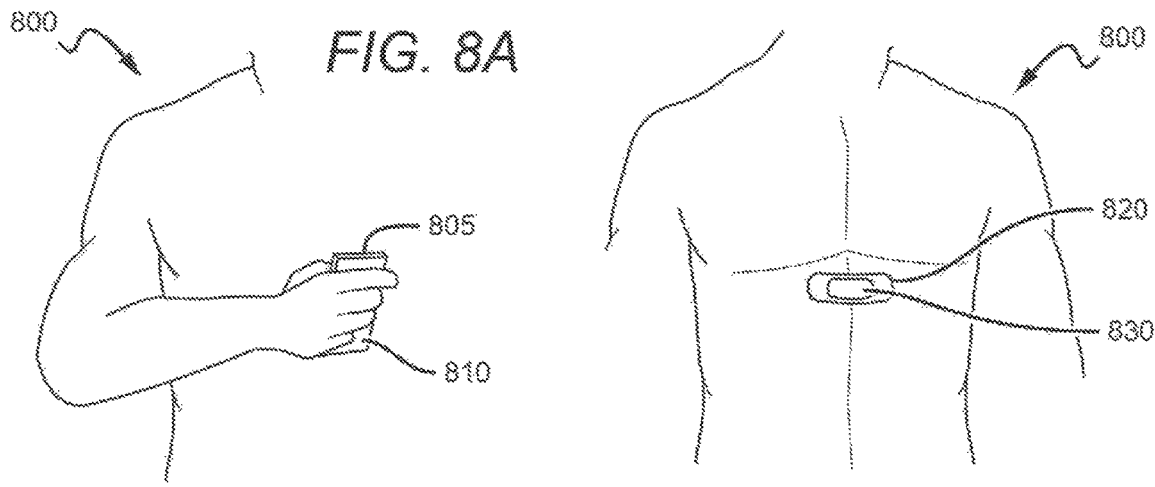
FIG. 8A
FIG. 8B
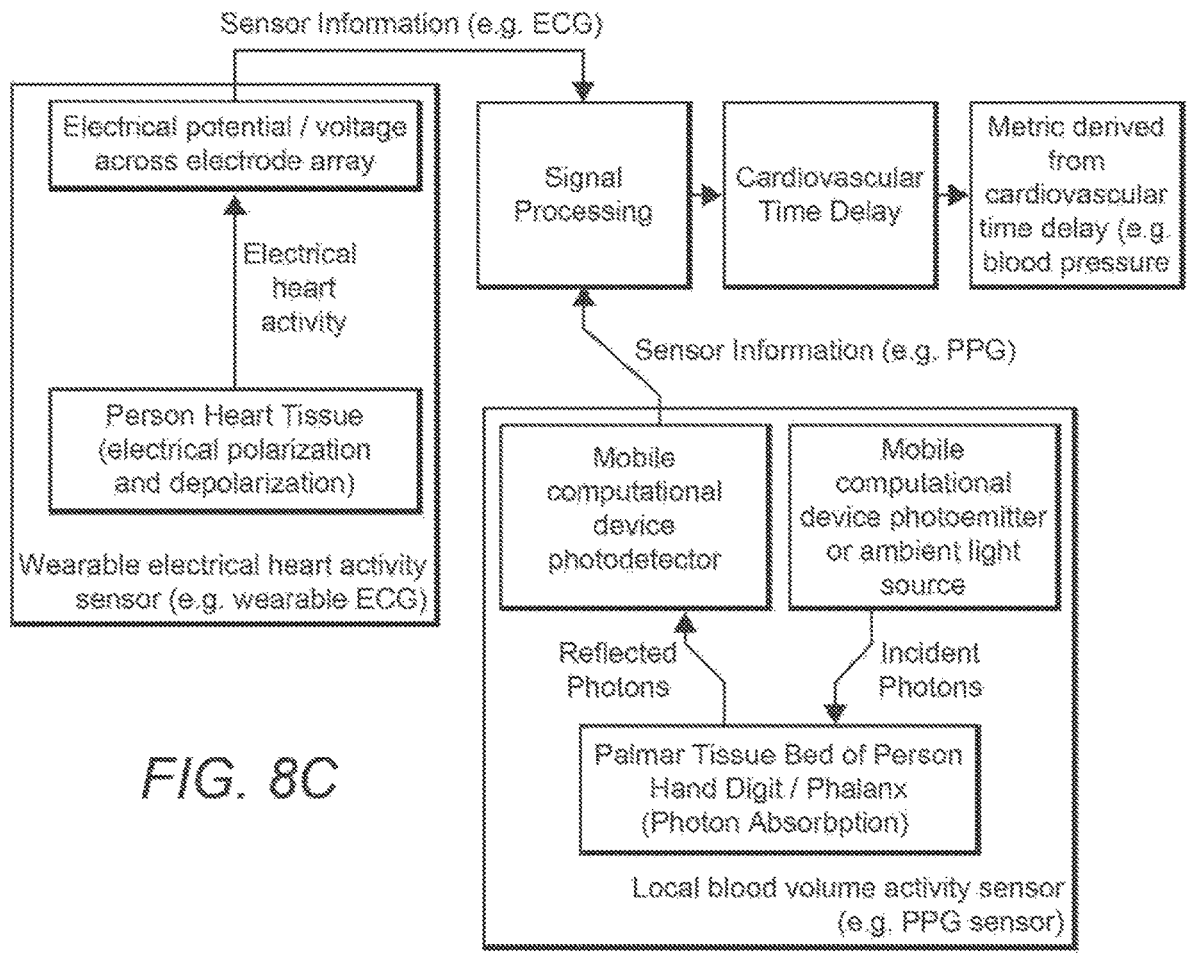
FIG. 8C

METHOD FOR COLLECTION OF BLOOD PRESSURE MEASUREMENT

This application claims priority to U.S. patent application Ser. No. 14/550,816 filed Nov. 21, 2014, which claims priority to U.S. Provisional Patent Application No. 61/909,661 filed Nov. 27, 2013, U.S. Provisional Patent Application No. 61/914,335 filed Dec. 10, 2013, and U.S. Provisional Patent Application No. 61/948,947 filed Mar. 6, 2014. Where a definition or use of a term in a reference that is incorporated by reference is inconsistent or contrary to the definition of that term provided herein, the definition of that term provided herein is deemed to be controlling.

FIELD OF THE INVENTION

The present invention relates to methods and systems for providing blood pressure value of a person. In particular, the present invention relates to methods and systems that can use one or more sensors housed in mobile devices or wearable devices.

Background

The following description includes information that may be useful in understanding the present invention. It is not an admission that any of the information provided herein is prior art or relevant to the presently claimed invention, or that any publication specifically or implicitly referenced is prior art.

In the United States, as of 2014, 78 million American adults, which correspond to about one-third of the American adult population, have high blood pressure. However, less than half of those adults with high blood pressure have their condition under control. Another one third of American adult population has pre-hypertension, in which blood pressure numbers are higher than normal, but not yet in the high blood pressure range. High blood pressure costs the nation $47.5 billion each year. This total includes the cost of health care services, medications to treat high blood pressure, and missed days of work. Since 1999, more people with high blood pressure, especially those 60 years old or older, have become aware of their condition and gotten treatment. Unfortunately, approximately 1 in 5 U.S. adults with high blood pressure still do not know that they have the condition.

Both invasive methods and noninvasive methods have been used to measure patients' blood pressure. Sphygmomanometer is one of the commonly used noninvasive devices to measure blood pressures. To begin blood pressure measurement, a user should use a properly sized blood pressure cuff. The cuff is wrapped around the upper arm of the person in a comfortable position. The blood pressure of the person is measured during the period that the cuff is rapidly inflated and deflated, while a healthcare provider listens to the sound of knocking for the person's systolic pressure with the stethoscope and simultaneously observes the sphygmomanometer. However, because of its size and complicated method of use, measuring blood pressure with sphygmomanometers may not be a convenient method for people who desire to measure blood pressure during work, exercise, or travel.

Many efforts have been put forth to make a method of the blood pressure measurement more convenient and user friendly. For example, U.S. Patent Application No. 2013/0072145 to Dantu discloses a method for differential estimation of blood pressure using two mobile phones. In this method, one mobile phone is used to record heart sound, and the other mobile phone is used to record video data from the finger-tip of the subject. Signals recorded from two different mobile phones are synchronized by a synchronization protocol, such as Master-Slave architecture or master time stamp. However, this method only contemplates a combination of sound and visual signals and absolutely requires the use of two separate mobile phones.

In another example, U.S. Patent Application No. 2005/0228299 to Banet discloses a method of monitoring vital signs of patient over a wireless network. In Banet, the monitoring device comprises an adhesive patch sensor that makes a trans-dermal, optical measurement of the time-dependent dynamics of blood flowing in an underlying artery. However, Banet's method also fails to contemplate the use of other types of sensors to measure blood pressure of the patient and requires the compression of the person's artery to restrict blood flow. All publications identified herein are incorporated by reference to the same extent as if each individual publication or patent application were specifically and individually indicated to be incorporated by reference.

Thus, there is still a need for an improved method to measure blood pressure noninvasively using various sensors, which is easy to use and provides accurate blood pressure data to a user.

SUMMARY OF THE INVENTION

The inventive subject matter provides systems and methods for measuring blood pressure of a person. One aspect of the invention is the method to measuring a person's blood pressure. The method comprises a step of providing a software configured to obtain a first sensor information from a first sensor and a second sensor information from a second sensor near simultaneously. The first sensor information comprises a first data point, and the second sensor information comprises a second data point. The method further comprises a step of deriving a first data feature based on the first data point and a second data feature based on the second data point. Based on the first data feature and the second data feature, a time delay value can be derived, which is correlated to a blood pressure value of the person. Based on the correlation between the time delay and the blood pressure, the blood pressure value of the person is derived and provided to a user.

Other aspects of the invention includes a system of measuring blood pressure of a person. The system includes sensors: a first sensor providing a first sensor information, and a second sensor providing a second sensor information. The system further comprises a computer system with a processor, which is configured to execute a software stored on a non-transient computer-readable memory. The software can activate the first sensor and the second sensor, and synchronize the first and second sensor information by obtaining the first and second sensor information near simultaneously. The first sensor information comprises a first data point, and the second sensor information comprises a second data point. The software is further configured to derive a first data feature based on the first data point and a second data feature based on the second data point. Based on the first data feature and the second data feature, the software is configured to derive a time delay, which is correlated to a blood pressure value of the person. Then, the software can derive a blood pressure value of the person based on the time delay.

Another aspect of the invention includes a method of measuring a cardiovascular time delay of a person. The method comprises a step of providing a software, which is configured to obtain a first sensor information from a first sensor, and a second sensor information from a second sensor near simultaneously. The first sensor information comprises a first data point, and the second sensor information comprises a second data point. The software is further configured to derive a first data feature based on the first data point and a second data feature based on the second data point. Then, based on the first data feature and the second data feature, a cardiovascular time delay can be derived. The method further comprises a step of providing a user the cardiovascular time delay value or a metric derived from the cardiovascular time delay of the person.

Another aspect of the invention includes a system which measures a cardiovascular time delay of a person. The system includes a first sensor providing a first sensor information, and a second sensor providing a second sensor information. The system further comprises a computer system with a processor, which is configured to execute a software stored on a non-transient computer-readable memory. The software can activate the first sensor and the second sensor, and synchronize the first and second sensor information by obtaining the first and second sensor information near simultaneously. The first sensor information comprises a first data point, and the second sensor information comprises a second data point. The software is further configured to derive a first data feature based on the first data point and a second data feature based on the second data point. Based on the first data feature and the second data feature, the software is configured to derive a cardiovascular time delay of the person. Then, the software can provide a user the cardiovascular time delay value or a metric derived from the cardiovascular time delay of the person.

Another aspect of the invention includes a method of measuring a blood pressure of a person using at least three sensors. This method comprises a step of providing a software, which is configured to obtain a first sensor information from a first sensor, a second sensor information from a second sensor, and a third sensor information from a third sensor near simultaneously. The first sensor information comprises a first data point, the second sensor information comprises a second data point, and the third sensor information comprises a third data point. The software is further configured to derive a first data feature based on the first data point, a second data feature based on the second data point, and a third data feature based on the third data point. Then, the software is configured to derive a first time delay based on the first data feature and the second data feature, a second time delay based on the first data feature and the third data feature, and a third time delay based on the second data feature and the third data feature. Among three time delays obtained based on the first, second, and third data features, at least two of the first, second, and third time delays are correlated to a blood pressure value of the person. Based on the correlations among the first, second and third time delays and the blood pressure, the software is configured to derive a blood pressure value of the person. The method further comprises a step of providing a user the blood pressure value of the person.

Another aspect of the invention includes a method of measuring blood pressure of a person by making a skin acoustic duct seal. In this method, a user is instructed to contact an opening of an acoustic duct of a device with the person's chest to create a skin acoustic duct seal. The method further comprises a step of providing a software, which is configured to obtain a first sensor information from a first sensor, wherein the first sensor information is an acoustic information transmitted via the acoustic duct and the acoustic information comprises a first data point, and a second sensor information from a second sensor. The second sensor information comprises a second data point obtained near simultaneously with the first sensor information, and second sensor information comprises a second data point. The software is further configured to derive a first data feature based on the first data point, and the second data feature based on the second data point. Based on the first and second data features, a time delay can be derived, which is correlated with the blood pressure of the person. Then, the blood pressure value can be derived based on the time delay. The method further comprises as step of providing a user the blood pressure value of the person.

Another aspect of the invention includes a method of measuring a cardiovascular time delay of a person by making a skin acoustic duct seal. In this method, a user is instructed to contact an opening of an acoustic duct of a device with the person's chest to create a skin acoustic duct seal. The method further comprises a step of providing a software, which is configured to obtain a first sensor information from a first sensor, wherein the first sensor information is an acoustic information transmitted via the acoustic duct and the acoustic information comprises a first data point, and a second sensor information from a second sensor. The second sensor information comprises a second data point obtained near simultaneously with the first sensor information, and second sensor information comprises a second data point. The software is further configured to derive a first data feature based on the first data point, and the second data feature based on the second data point. Based on the first and second data features, a cardiovascular time delay can be derived. The method further comprises as step of providing a user the cardiovascular time value or a metric derived from the cardiovascular time delay of the person. This metric includes blood pressure.

Another aspect of the invention includes a method of measuring blood pressure of a person by using two visual sensors. In this method, a user is instructed to point a first photodetector of a device at a portion of the person's body. The method further comprises a step of providing a software, which is configured to obtain a first sensor information from a first sensor and a second sensor information from a second sensor near simultaneously with the first sensor information. The first and second sensors comprise the first and second photodetectors. The first sensor information comprises a first data point, and the second sensor information comprises a second data point. The software is further configured to derive a first data feature based on the first data point and a second data feature based on the second data point. Based on the first data feature and the second data feature, the software can derive a time delay, which is correlated to a blood pressure value of the person. Then the software can derive a blood pressure value of the person based on the time delay. The method further comprises a step of providing a user the blood pressure value of the person.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 4A-C illustrate one exemplary embodiment of blood pressure measurement by making a skin acoustic duct seal and recording phonocardiograms. FIG. 4A illustrates a perspective view of the product housing for a mobile computational device. FIG. 4B illustrates aside view of the product housing for the mobile computational device. FIG. 4C illustrates a schematic view of measuring acoustic heart activity on the person's chest.

FIG. 5A illustrates a schematic view to measure blood pressures using ballistocardiogram and a plethysmogram signals. FIG. 5B illustrates a schematic diagram to process ballistocardiogram and a plethysmogram signals.

FIG. 6A illustrates a schematic view to measure blood pressures using two plethysmograms. FIG. 6B illustrates a schematic diagram to process two PPG signals.

FIG. 7A illustrates a schematic view to measure blood pressure using two plethysmograms. FIG. 7B illustrates a schematic diagram to process two PPG signals.

FIGS. 8A-C illustrate one exemplary embodiment of blood pressure measurement by using a mobile computational device and a patch to record a plethysmogram and an electrocardiogram. FIG. 8A illustrates a schematic view to measure blood pressure using a mobile computational device. FIG. 8B illustrates a schematic view to measure blood pressure using a patch. FIG. 8C illustrates a schematic diagram to process ECG signal and PPG signal.

FIG. 9A illustrates a schematic view to measure blood pressure using two wearable devices.

FIG. 9B illustrates schematic diagrams to process ECG signal and PPG signal.

FIG. 10A illustrates a schematic view to measure blood pressure using one wearable device. FIG. 10B illustrates schematic diagrams to process ECG signal and PPG signal.

FIG. 11A illustrates a schematic view to measure blood pressure using one wearable device. FIG. 11B illustrates a schematic diagram to process BCG signals and PPG signals.

FIG. 12A illustrates a schematic view to measure blood pressure using one mobile device. FIG. 12B illustrates a schematic diagram to process ECG signal and PPG signal.

DETAILED DESCRIPTION

Figure 1:
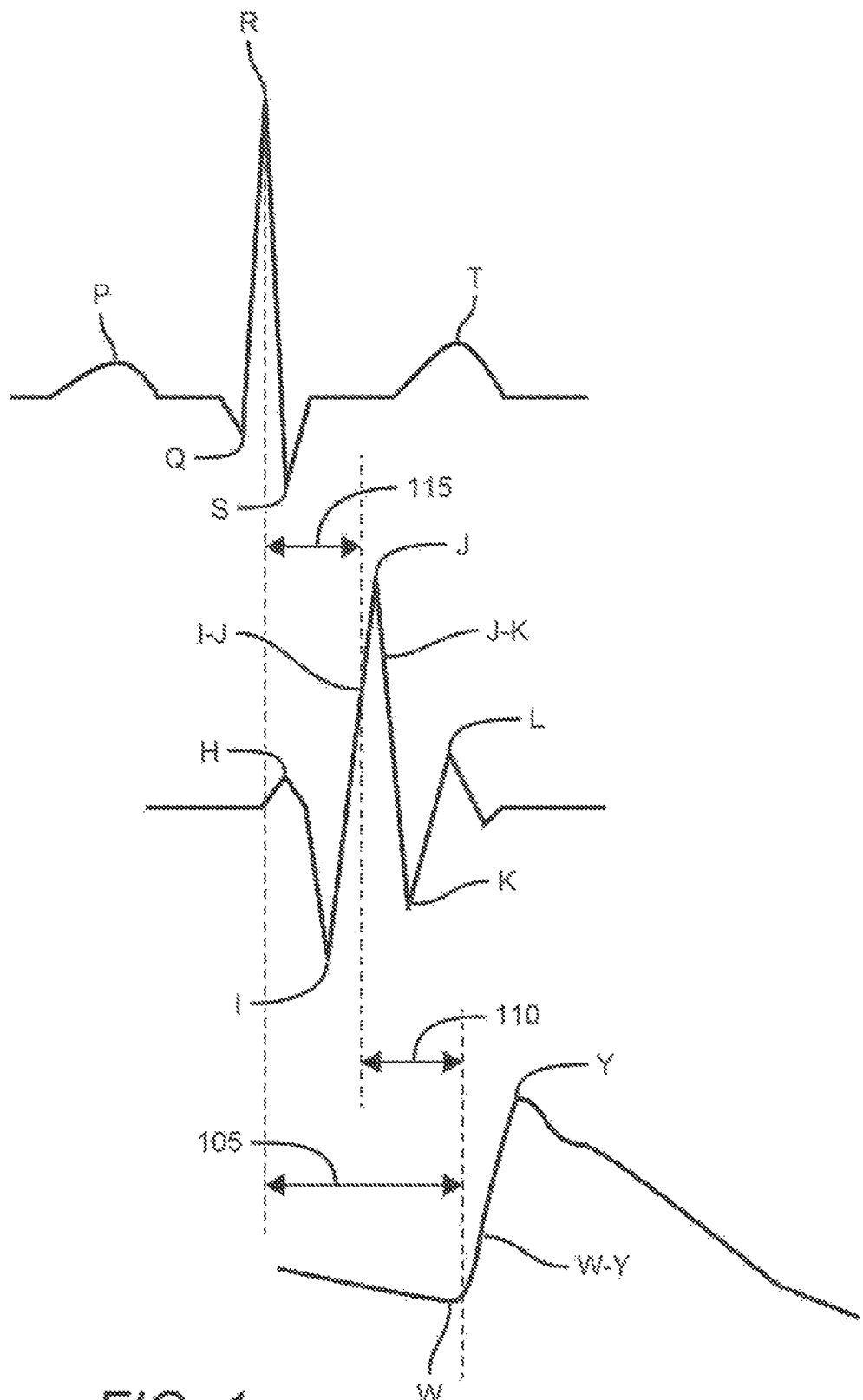
FIG. 1 illustrates diagrams of three different sensor signals for a heartbeat.

The present invention relates to methods and system for measuring and providing blood pressure of a person. The principles and operations for such methods and systems, according to the present invention, may be better understood with reference to the accompanying description and drawings.

It should be noted that any language directed to a computer should be read to include any suitable combination of computing devices, including servers, interfaces, systems databases, agents, peers, engines, modules, controllers, or other types of computing devices operating individually or collectively. One should appreciate that computing devices comprise a processor configured to execute software instructions stored on a tangible, non-transitory computer readable storage medium (e.g., hard drive, solid state drive, RAM, flash. ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C. or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities or ranges, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention am approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

One aspect of the present invention includes a method of measuring blood pressure of a person using one or more devices operated by one or more software. The software is configured to obtain sensor information from a sensor. In a preferred embodiment, a sensor is a hardware sensor on a mobile device (e.g., a cell phone, a smart phone, a handheld computer, an PAD, and a PDA, etc.). In some embodiments, it is contemplated that a sensor is a hardware sensor on a wearable device (e.g., a chest strap, a watch, an eyeglasses, a headphone, a hat, a helmet, a glove, an armband, a headband, a headset, a wristband, an ankle band, a cloth, a ring, and a toe cap, etc), or a patch (e.g., a partially disposable patch, a wholly disposable patch, a non-disposable patch, a fabric patch, a plastic patch, and a metal patch, etc.).

It is generally preferred that the mobile device, the wearable device, or the patch comprises an embedded electrical system, a power source, and a product housing. The embedded system further comprises an electrical hardware circuit consisting of a digital controller, an analog-to-digital converter, a non-transient computer-readable memory (e.g., a hard drive, a flash drive, RAM, etc.). The non-transient computer-readable memory stores a software, which is uploaded to at least one or more processing units (e.g., processors, processing cores, digital controllers, etc.). The software is responsible for driving hardware components to accomplish the defined tasks (e.g., controlling sensor functionality, capturing sensor signals, activating sensors, etc.).

Many types of sensors embedded in or coupled with the mobile device, the wearable device, or the patch, can be used to obtain sensor information. In a preferred embodiment, sensors may include an acoustic-to-electrical transducer (e.g., microphone), an accelerometer, an array of electrodes having at least two electrodes, a photodetector (e.g., a light sensor, an image sensor, a semiconductor charge-coupled device (CCD), an active pixel sensor in complementary metal-oxide-semiconductor (CMOS), a N-type metal-oxide-semiconductor (NMOS, live MOS), etc.). However, it is also contemplated that other types of sensors can be used to obtain sensor information. For example, sensors may include a chemical sensor, a magnetic sensor, a moisture sensor, a pressure sensor, a thermal sensor, a presence sensor, and any other types of sensors suitable for obtaining information related to blood pressure.

Each type of sensor may provide different type of sensor information in relation to a person's blood pressure. For example, an acoustic-to-electrical transducer embedded in, or placed at the mobile device, the wearable device, or the patch, can provide sensor information of the acoustic heart activity in a form of phonocardiogram (PCG). The turbulent closure of heart valves cause acoustic perturbations that can be detected with a proper acoustic transducer (e.g., stethoscope). The acoustic heart activity trace captured by the acoustic-to-electrical transducer contains physiological information about the occurrence of the closure of the atrioventricular and semilunar valves of the person's heart as well as physiological information about the timing related to the ejection of blood from the left ventricle of the heart into the aorta and peripheral arterial tree.

To record a PCG signal, the software activates the acoustic-to-electrical transducer. Incident, analog acoustic waves of the acoustic heart activity induce fluctuations in outputted electrical activity of the acoustic-to-electrical transducer. This electrical output is digitized via a dedicated analog-to-digital converter component, an analog-to-digital converter equipped digital controller component, or any hardware component within the embedded electrical system equipped with the ability to convert an analog electrical signal into a discretely sampled digital signal.

A PCG signal can be generally represented as a waveform. Each waveform is associated with a single cardiac cycle. Signal peak detection and common bandpass signal processing techniques are used to isolate the frequencies of interest in the acoustic heart activity trace signal, particularly those below 1000 Hz, and used to identify the precise time reference associated with left ventricular contraction and blood ejection from the heart into the aorta for a single cardiac cycle.

In a preferred embodiment, the device includes an accelerometer to record mechanical heart activity. The mechanical heart activity trace captured by the accelerometer contains physiological information about the mechanical, cardiac contraction event, generally represented as a form of the ballistocardiogram (BCG). A single cardiac cycle involves the mechanical contraction of the ventricles which generate the largest mechanical force during a single cardiac cycle. The BCG is a measure of the mechanical forces generated by mechanical activities of the heart, which include the transient contraction of cardiac muscle and ejection recoil forces of the blood being ejected from the ventricles into the aorta and pulmonary artery. The mechanical force waves can be passed through the body tissue and can be strongly detected in the area closest to the heart and are also detectable at the head and ear. A preferable, but by no means only, way to place an accelerometer for left ventricular contraction force detection is by coupling the product housing with the chest of the person closest to the apex of the heart, where the heart is closest to the skin and where the left ventricle is located. Proper signals can be acquired elsewhere on the chest of the person or at other locations on the surface of the body where proper mechanical coupling of product housing can be achieved.

In a preferred embodiment, a mobile computational device contains an embedded system that includes an electrical circuit comprising a MEMS-based accelerometer. The electrical circuit is fastened or mechanically fixed to the product housing of the mobile computational device such that a force vector applied to the product housing is equally applied to the accelerometer. A software uploaded to the digital controller of the embedded system handles the accelerometer sensor updates and is provided with at least the X, Y, Z components of acceleration from the accelerometer. The component of acceleration (either the X, Y, or Z component) that is relatively orthogonal to the chest plane where contact with the mobile computational device is made is used for data capture and the remaining other two signal components may or may not be used for data capture. The selection for the components of acceleration may be dependent on the configuration of the accelerometer, the relative orientation of the accelerometer to the product housing, and the relative position of the product housing to the chest plane of the person when the product housing is in contact with the person's chest.

Middle waveform shown in FIG. 1 shows an example of the BCG waveform. A BGC waveform is almost entirely a result of ventricular mechanical activity of the heart when it is properly measured at the appropriate location on the chest or other body surface (e.g., head or ear) with an accelerometer equipped mobile computational device with sufficient mechanical coupling between the chest (or body surface) and the device. For example, the values of the J-K "max" negative slope or a J amplitude threshold are dependent on the ventricular mechanical activity of the heart. In addition, the amplitude of the J peak is proportional to the force of ventricular contraction. The HL interval correlates well with the total time of ventricular ejection, which represents the total time that blood is being ejected into the aorta. Furthermore, the onset of H represents the beginning of the blood ejection from the ventricles and the commencement of L represents the end of blood ejection from the ventricles. Thus, the amplitude of the peak of the component of acceleration selected for each ventricular cardiac contraction event is proportional to the contractile force of the heart and stroke volume. A component of acceleration (e.g., a peak acceleration, a max positive change in acceleration, a max negative change in acceleration, etc.) selected for each ventricular cardiac contraction event is selected and the time at which it occurs serves as the time reference for the left ventricular contraction event or time of blood ejection from the heart.

In some embodiment, an array of electrodes can be used to obtain sensor information of relevant to a person's blood pressure. An array of electrodes embedded in, or placed on the mobile device, the wearable device, or the patch, can provide sensor information of electrical heart activity in a form of electrocardiogram (ECG). The electrical heart activity trace contains physiological information about the occurrence of the electrical polarization and depolarization of cardiac tissue.

Upper waveform shown in FIG. 1 shows an example of the ECG waveform. The electrical activity of the heart can be detected with a pair of electrodes placed in contact with the surface (e.g., skin, etc.) of the body. Improved electrical heart activity detection is achieved with electrode placement wherein each electrode is placed on the surface (e.g., skin, etc.) of the body such that the electrical potential path through the body between the electrode pair crosses the path of the heart. Signal peak detection, represented as the peak of the waveform, R, can be used to identify a precise time reference associated with electrical systole and subsequent left ventricular mechanical contraction of the heart.

In some embodiments, a photodetector can be used to obtain sensor information relevant to a person's blood pressure. A photodetector embedded in, or placed at the mobile device, the wearable device, or the patch, can provide sensor information in a form of photoplethysmogram (PPG). The software activates the photodetector and an incident light source (e.g., camera flash, etc.), if available. Ambient light may be used in place of an incident light source in some embodiments. The photodetector and incident light source, if included, are either in direct contact with the skin of a regional tissue of interest or aimed at the skin of a regional tissue of interest.

Human blood contains intrinsic biophysical properties in which it absorbs incident light photons. With each cardiac contraction, an arterial pressure wave is generated and propagated along the arterial tree to the periphery of the cardiovascular system, reaching the microvasculature of the subcutaneous and dermal tissue of the skin. Thus, periodic cardiac contractions lead to localized increases to blood volume at the person's regional tissue of interest; for example, the palmar tissue bed of the digit, in contact with the photodetector. These localized increases to blood volume cause more light to be absorbed and less light to be reflected back to the photodetector. Because larger volumes of blood absorb greater amounts of incident light photons, changes in subcutaneous and dermal tissue blood volume can be detected with a photodetector aimed at or in direct contact with the subcutaneous and dermal tissue bed of interest. Thus, the photoplethysmogram represents the local tissue blood volume activity trace, which contains physiological information about the pulsatile fluctuations of blood volume present in the micro-vasculature and capillary beds of a region of tissue near the surface of the body.

Incident, analog fluctuations in reflected light from the regional tissue of interest; for example, the palmar tissue bed of the person's digit, in contact with or aimed at the photodetector induce either 1) fluctuations in outputted electrical activity of the photodetector, which is subsequently digitized via a dedicated analog-to-digital converter component, an analog-to-digital converter equipped digital controller component, or any hardware component within the embedded electrical system equipped with an analog to digital converter) or 2) fluctuations in the individual color components (e.g., RGB components) of pixels from an image sensor type photodetector.

The local tissue blood volume activity in a form of PPG can be captured on a tissue area on a person's body for contact with the photodetector. The point of contact can be any other location on the surface of the body at a sufficient cardiovascular distance from the heart or a sufficient difference in cardiovascular distance from the heart from another photodetector. Signal strength (e.g., pulsatile blood volume signals) is stronger near the termination of the arterial tree such as near the fingers and toes.

Bottom waveform shown in FIG. 1 shows an example of a PPG or IPG signal as a waveform. Each waveform is associated with the arrival of an arterial pressure wave generated from a single cardiac cycle, which is represented by a single left ventricular contraction of the heart. Each waveform has a foot of the waveform W, a point of maximum slope of the waveform W-Y, and a peak of the waveform Y.

In some embodiments, local tissue blood volume signals can be detected using an array of electrodes. Impedance plethysmography (IPG), which may also be referred to as electrical plethysmography, electrical impedance plethyamography, or bioimpedance plethysmography, is a non-invasive method for capturing localized blood volume changes in a regional tissue of interest. In practice, it usually involves placing electrodes in direct skin contact at the tissue region of interest and measuring changes in electrical potential of the tissue while driving a small current of electricity through the tissue. Blood is an ionic conductor, which permits the flow of electrical current in one or more directions. Thus, electrical current can flow better through blood than other tissues of the body. Therefore, the more the blood there is in a tissue segment, the greater the conductivity of that tissue segment, and the lesser the impedance of that tissue segment. IPG can be used to detect arterial blood pulse waves. With each propagating pulse wave through an artery in a given tissue segment, there is a transient increase in blood volume in that tissue segment that causes a transient change in the impedance of that tissue segment, which is measured using the sensing electrodes of the IPG sensor.

To capture an IPG signal, an array of current electrodes or driving electrodes are placed in direct contact with the skin of the tissue region of the person and are used to drive a low-amplitude AC current. An AC electrical current is used usually within the frequency range of 20-100 kHz through the said tissue region of the person. An array of measurement electrodes, sometimes referred to as sensing electrodes or voltage electrodes, are also placed in direct contact with the skin of the tissue region of the person, usually between the current electrodes, and are used to measure the frequency-dependent AC potential through the regional tissue of the person.

It is preferred that the array of current electrodes is in a different array of electrodes as the measurement electrodes. In some embodiments, either 2 or 4 total electrodes can be used in the hardware configuration of an IPG sensor. If the array of current electrodes is the same as the array of measurement electrodes and there are 2 electrodes in total, then the hardware configuration is a 2-electrode or bipolar configuration. If the array of current electrodes is different than the array of measurement electrodes and there are 4 electrodes in total then the hardware configuration is a 4-electrode or tetrapolar configuration.

It is preferred that a single waveform in the sensor information corresponds to a single data point of the sensor information. However, it is also contemplated that a single waveform corresponds to more than two data points. Further, it is also contemplated that more than two waveforms correspond to a single data point.

In some embodiments, the sensor information comprises more than one data point. For example, PPG, PCG, or BCG can be recorded during a period of multiple cardiac cycles, which is represented as multiple waveforms. Generally, only one data point from each sensor is required to derive the blood pressure value of the person. However, in some embodiments, it is contemplated that more than one data points are used from one sensor is used to derive the blood pressure value of the person.

Each data point in the sensor information can be represented by one or more features of the waveform. Some features of the waveform include a peak of the waveform, a foot of the waveform, a point of maximum slope of the waveform, a point of minimum slope of the waveform, a time to peak of the waveform, a width of the peak, a peak of the first or second derivative of the waveform, a foot of the first or second derivative of the waveform, a point of maximum slope of the first or second derivative of the waveform, and a point of minimum slope of the first or second derivative of the waveform. Any other features of the waveform that can be derived from the waveform by an ordinary person in the art are also contemplated to be used to represent the data point.

When more than one sensor information for a single cardiac cycle is detected or recorded by one or more types of sensors, a correlation between two or more sensor information can provide more detailed information for a more accurate measurement of the blood pressure. FIG. 1 shows examples of time delays 105, 110, 115. For example, the time difference 105 between the onset of R of the ECG to the onset of W of the PPG or IPG represents a time delay or pulse arrival time that correlates to a systolic pressure. However, the pulse arrival time does not correlate as significantly with a diastolic pressure because it includes a time delay known as the pre-ejection period, which is the time delay from electrical to mechanical systole of the heart during a single cardiac cycle. The addition of the BCG to the ECG and PPG or IPG enables the capture of the time difference 115 between the peak amplitude R of ECG to the max positive slope 14 of BCG, which correlates with a pre-ejection period. Furthermore, the time difference 110, or pulse transit time, between the max positive slope I-J of BCG and onset of W of the PPG correlates with a diastolic pressure.

When two or more sensor information is obtained and used for deriving blood pressure value, it is preferred that those sensor information are synchronized together so that the data points from those sensor information correspond to the same cardiac cycle. It is contemplated that there are two methods to synchronously capture sensor data: 1) using an embedded system design that enables the synchronous retrieval of the latest sensor values from asynchronously updating sensors, and 2) using an embedded system design that enables the synchronous retrieval of the latest sensor values and system clock time stamps. The final output of both methods is the session time-synchronized signal traces, which can be passed on for further processing. Note that the "buffer" used herein refers to a "data buffer" which refers a region of physical memory storage used to temporarily store data.

Figure 2:
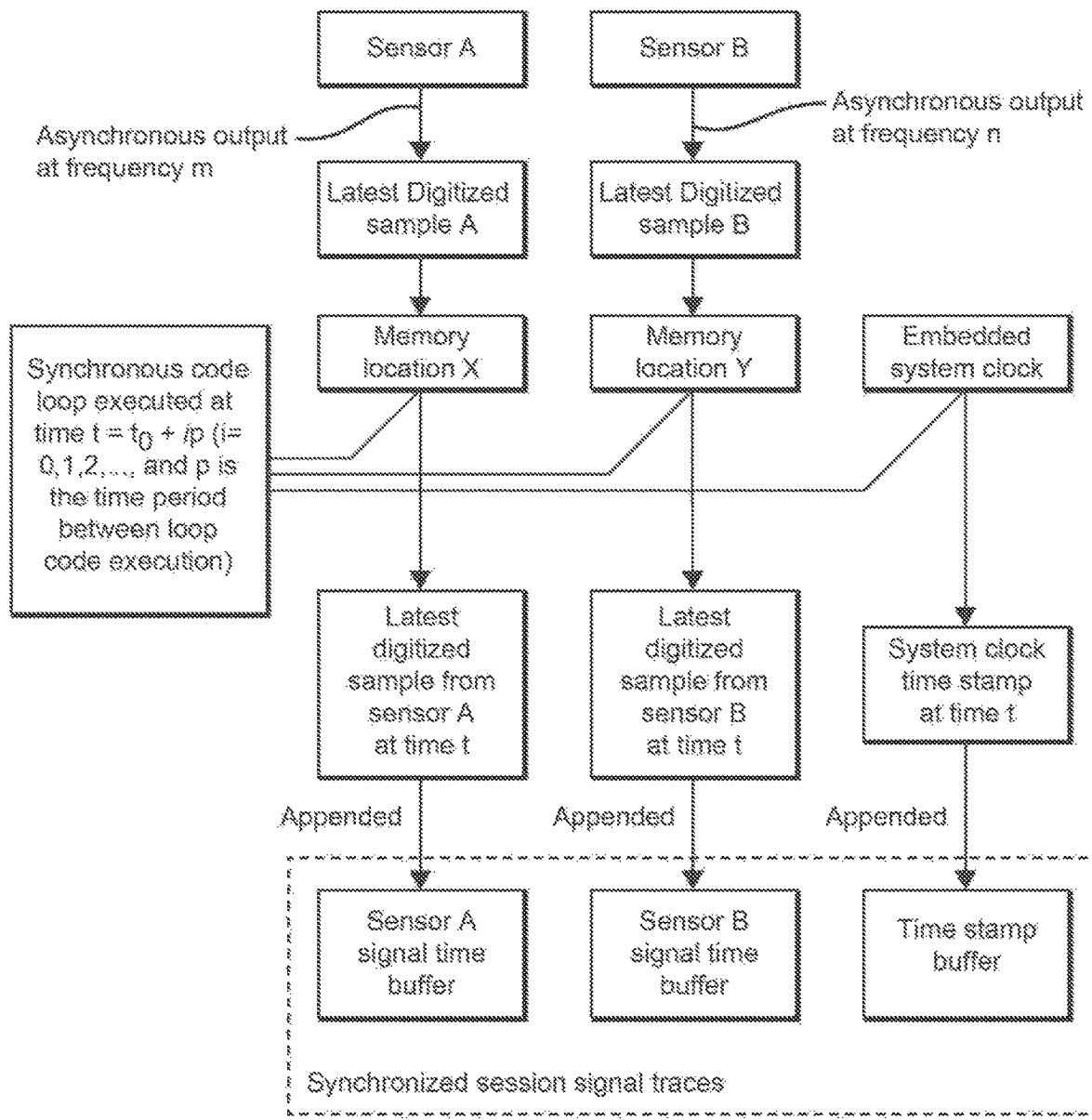
FIG. 2 illustrates a diagram of synchronous retrieval of the latest sensor values from asynchronously updating sensors.

The first method to synchronously capture sensor data is described in FIG. 2. In this method, asynchronously updating sensor data can be near simultaneously captured. This method of synchronization is useful to measure blood pressure using a single mobile computational device. The software running on the digital controller of the embedded system of the mobile computational device, initiates a measurement session of which initiation is triggered by user interaction with the mobile computational device. Periodic sampling of digitized sample A (e.g., a plethysmogram) using sensor A (e.g., a photodetector) is conducted at a frequency m, and another periodic sampling of digitized sample B (e.g., phonocardiogram information) using sensor B (e.g., an acoustic-to-electrical transducer) is conducted at a different frequency n. Thus, digitized sample A and sample B are updated asynchronously.

The software allocates memory space within the embedded system, either on a memory-equipped digital controller component or dedicated memory component, to hold in memory slots for: 1) the most recent digital value of the acoustic-to-electrical transducer (memory location X), 2) the most recent digital value of the photodetector (memory location Y), and 3) the session signal trace buffer.

It is preferred that the digitized sample A and sample B are constantly updated. The latest update of the digitized sample B, for example, outputs of the acoustic-to-electrical transducer, which is the latest acoustic digital value, is routed into and handled by the software where a specific thread or loop of code is responsible for receiving the latest acoustic digital values. The latest update of the digitized sample A, for example, outputs of the photodetector, either in the form of frames comprised of pixels each pixel of which is comprised of an red, green, and blue component for an image-type photodetector or single-value intensity values, the latest photodetector digital value, is also routed into and handled by the software where a specific thread or loop of code is responsible for receiving the latest photodetector digital values.

Every time the latest acoustic digital value is routed into and handled by the software, it is stored in memory as the most recent digital value of the acoustic-to-electrical transducer. Similarly, every time the latest photodetector digital value is routed into and handled by the software, it is stored in memory as the most recent digital value of the photodetector.

In asynchronous periodic fashion, the software runs another thread or loop of code that is responsible for retrieving the most recent digital value of the acoustic-to-electrical transducer stored in memory and the most recent digital value of the photodetector stored in memory. At the same time, the software generates a time stamp, as precise as possible, but ideally precise to less than or equal to one millisecond. However it is contemplated that the time stamp can be generated at an interval of less than 1 millisecond, less than 5 milliseconds, less than 10 milliseconds, less than 50 milliseconds, or less than 100 milliseconds. The latest digitized sample from sensor A, sensor B, and system clock timestamp at time t are appended to the session signal trace buffer in memory, generating a synchronized set of parallel physiological signal traces.

Figure 3:
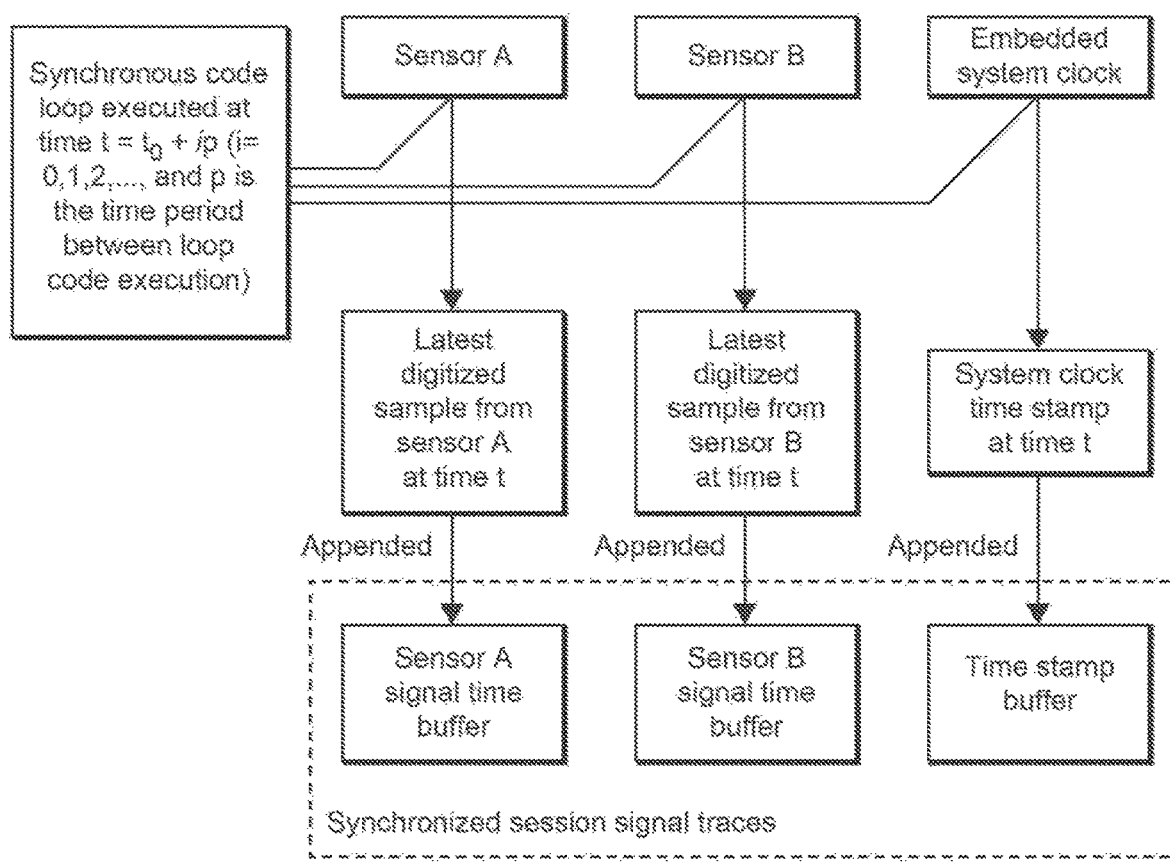
FIG. 3 illustrates a diagram of synchronous retrieval of latest sensor values and system clock time stamps.

The second method to synchronously capture sensor data is described in FIG. 3. In this method, periodic sampling digitized sample A (e.g., plethysmogram) using sensor A (e.g., a photodetector) and another digitized sample B (e.g., phonocardiogram information) using sensor B (e.g., an acoustic-to-electrical transducer). The most recent digital value of the sample A and sample B are near simultaneously captured. As the frequency of capturing the digital value of the sample A and sample B is much shorter than the frequency of the cardiac cycle (e.g., less than 1 millisecond, less than 5 millisecond, less than 10 millisecond, less than 50 millisecond, less than 100 millisecond, etc.), near simultaneously captured the digital value of the sample A and sample B are likely to correspond to the same cardiac cycle (e.g., a single heartbeat).

In a synchronous periodic fashion, the software runs another thread or loop of code that is responsible for retrieving the most recent digital value of the acoustic-to-electrical transducer stored in memory and the most recent digital value of the photodetector stored in memory. At the same time, the software generates a time stamp, as precise as possible, but ideally precise to one millisecond. However it is contemplated that the time stamp can be generated at an interval of less than 1 millisecond, less than 5 milliseconds, less than 10 milliseconds, less than 50 milliseconds, or less than 100 milliseconds. The latest digitized sample from sensor A, sensor B, and system clock timestamp at time t are appended to the session signal trace buffer in memory, generating a synchronized set of parallel physiological signal traces.

In some embodiments, it is also contemplated that a synchronization method using a time stamp can be used to synchronize asynchronously captured digital value of the sample, in this method, all changes to the asynchronously captured digital values are marked with time stamps. Synchronization proceeds by transferring all asynchronously captured digital values with a time stamp later than the previous synchronization.

In addition, it is also contemplated that the synchronization of sensor information can be conducted via synchronizing the time stamp between two devices. One of the methods contemplated herein is the periodic inaudible, high frequency sound synchronization method. This method can be used between two wireless devices. In this method, the first device contains a speaker and the second device contains a microphone. A synchronization process between the two devices is initiated. The synchronization process occurs at the beginning of each measurement session or at a sufficient interval to maintain a desired level of synchronicity between the two devices to avoid an undesirable level of clock drift. An inaudible high frequency sound pulse of a pre-determined frequency (e.g., 21 kHz) is emitted by the speaker of the first device. Simultaneous with the moment of emission of the sound pulse from the first device, the first device creates and stores a first time stamp on a memory location within the embedded system of the first device. The second device is programmed to look at a pre-determined frequency band that matches the pre-determined frequency of the sound pulse emitted by the speaker of the first device. Through the use of a continuous discrete Fourier transform (e.g., a fast Fourier transform) applied to the real-time stream of microphone sensor information from the microphone on the second device, the second device detects the precise moment of the amplitude of a pre-determined frequency band (e.g., a narrow band around 21 kHz) that reaches a pre-defined threshold. Simultaneous with the precise moment that the second device detects the precise moment the amplitude of a pre-determined frequency band (e.g., a narrow band around 21 kHz) that reaches a pre-defined threshold, the second device creates and stores a second time stamp on a memory location within the embedded system of the second device. At a later time, when the sensor information is wirelessly moved from the second device to the first device, the second time stamp is also moved onto the first device. A time delay is calculated between the first time stamp and the second time stamp is calculated. Whether the time delay is positive or negative, it is used to adjust the time-alignment of sensor information that is collected from both the first device and second device. It is important to note that a wide range of varying frequencies can be selected in the human inaudible range.

Another method of synchronizing the time stamp between two devices is the continuous inaudible, high frequency sound synchronization method. This method can be used between two wireless devices. In this method, the first device contains a microphone and the second device contains a speaker. A measurement session involving the two devices is initiated. The initiation process of the first device encompasses the first device activating the microphone. The first device also initiates recording sensor information from a sensor within the first device to a memory location within the embedded system of the first device. The second device activates a speaker and a sensor within the second device. The second device is programmed to emit high frequency sounds through its speaker within a human-inaudible frequency band (e.g., a finite number of frequencies within a range of 20-22 kHz). The frequency of sound emitted by the speaker on the second device at any time (t=x) is directly proportional to the value of the sensor information from the sensor on the second device at the same time (t=x). More specifically, a pre-determined number of numerical values are selected and mapped to a pre-determined finite number of frequency bands (e.g., a finite number of bands within a range of 20-22 kHz). The microphone of the first device captures the sound emitted by the speaker of the second device with a negligible delay caused by to the speed of sound travel. Through the use of a continuous discrete Fourier transform (e.g., a fast Fourier transform) applied to the real-time stream of microphone sensor information from the microphone of the first device, the first device detects the amplitude for each frequency band within the matched, pre-defined number of frequency bands selected (e.g., a finite number of bands within a range of 20-22 kHz) and whichever band whose amplitude exceeds a pre-defined threshold at some time t=y. Its center frequency is selected as the dominant frequency and is assumed to be the emission of the speaker of the second device. This frequency is then mapped, via the pre-defined mapping, to a numerical value whose numerical value is selected as the current value of the sensor of the second device at that time t=y. This value is used as the current, synchronized sensor value of the sensor on the second device at that time t=y and is stored on the first device in memory with the sensor information being generated by sensors on the first device. It is important to note that there is no significance to time t=y or t=x. Also, it is important to note that a wide range of varying frequencies can be selected in the human inaudible range.

Another method of synchronizing the time stamp between two devices is the periodic electromagnetic radio frequency synchronization method. This method can be used between two wireless devices. In this method, the first device and the second device contain electromagnetic radios (e.g., a Bluetooth® 2.4 GHz electromagnetic radio). A wireless connection is established between the first and second device using the connection protocol defined by the Bluetooth communication stack. The synchronization process occurs at the beginning of each measurement session or at a sufficient interval to maintain a desired level of synchronicity between the two devices to avoid an undesirable level of clock drift. The first device generates a first time stamp and stores it within a memory location within the embedded system of the first device. Simultaneously, a special request command—a special sequence of data that has a pre-determined meaning—is sent from the first device to the second device wirelessly over the electromagnetic radio frequency communication connection established between the two electromagnetic radios. The second device has been programmed to handle the receipt of the special request command. Upon receipt of the special request command, the second device generates a second time stamp with its internal clock and immediately responds with a special response over the electromagnetic radio frequency communication connection to the first device. The special response from the second device to the first device contains the second time stamp generated by the second device. The first device is programmed to handle the receipt of the special response from the second device. Once the special response from the second device is received, the first device stores the second time stamp, which was contained within the special response, in its memory in a fashion that associates it with the first time stamp. A time delay is calculated between the first time stamp and the second time stamp is calculated. When sensor information from the second device is aggregated with sensor information from the first device, the time delay is used to adjust the time-alignment of sensor information that is collected from both the first device and second device.

In a preferred embodiment, these synchronization methods can be used independently from each other. In some embodiments, it is contemplated that a combination of two or more of those synchronization methods can be used.

The sensor information in the form of a waveform can provide one or more data feature at one or more data point. The data feature may comprise a point on the waveform (e.g., an amplitude of a peak of the waveform, an amplitude of a foot of the waveform, etc.). The data feature may comprise a time reference (a time at the peak of the waveform, a time at the foot of the waveform, etc.) The time can be absolute time. In some embodiments, the time can be relative time.

From two or more data features of two or more sensor information, a value of time delay can be derived. In a preferred embodiment, the time delay is derived from a cross-correlation between the first data feature and the second data feature.

For example, as shown in FIG. 1, I-J of the BCG and W of the PPG or IPG are two data features from two different sensor information. The time difference 110 between the max positive slope of I-J of the BCG to the onset of W of the PPG or IPG represents the time delay or pulse transit time that correlates to a diastolic pressure. Likewise, the time difference 105 between the peak R of ECG to the onset W of PPG correlates with a systolic pressure.

Various values of time delays can be derived based on the data features and the type of signals. A Pulse Arrival Time (PAT) is the time delay between the time immediately after electrical systole of the heart and the arrival of an arterial pressure wave to a distance away from the heart. It is contemplated that PAT comprises a time difference between ECG and PPG signals, or a time difference between ECG and IPG signals.

Pulse Transit Time (PTT) is time delay between corresponding features of two cardiovascular waves where each wave relates to movement of blood within the arterial tree and where each wave is measured at different arterial distances from the heart and where each wave is measured with one of the following sensor information: PPG, IPG, BCG, and PCG. It is contemplated that PTT_A comprises a time difference between PCG and PPG. Pulse Transit Time B (PTT_B) is time delay between the mechanical left ventricular contraction/blood ejection from the heart into the aorta and the arrival of an arterial pressure wave to a distance away from the heart, or a time difference between BCG and PPG signals. It is contemplated that Pulse Transit Time C (PTT_C) comprises a time difference between two PPG signals.

PAT includes a delay known as the Pre-Ejection Period (PEP), which is the time delay between electrical systolic of the ventricles of the heart and mechanical left ventricular contraction/blood ejection from the heart into the aorta. The PEP for any individual varies with every heartbeat. Thus, Pulse Transit Time, which does not include the PEP, can provide a more accurate tool to measure blood pressure.

The time delay derived based on two time references is correlated with the blood pressure value. In some embodiments, it is contemplated that the blood pressure value and the time delay can be linearly correlated as a function of P=Mt+N, where P is a systolic or diastolic blood pressure, M and N are coefficients, t is a time delay (e.g., a pulse transit time). In other embodiments, it is contemplated that the blood pressure value and the time delay can be non-linearly correlated as a function of $P=Me^{-Nt}$, where P is a systolic or diastolic blood pressure, M and N are coefficients t is a time delay (e.g., a pulse transit time). In some other embodiments, it is also contemplated that the blood pressure value and the time delay can be sigmoidally correlated.

A non-linear mapping of pulse transit time of cardiovascular time delay to Pulse Wave Velocity is based on the correlation among the velocity, time, and distance, as a function of v=d/t, where v is pulse wave velocity, t is a time delay between two cardiovascular waves (e.g., a pulse transit time), and d is the arterial distance. For example, the time delay can be calculated based on the difference of two arterial distances from the heart, where each arterial distance from the heart is calculated by the distance from the heart to the location at which each cardiovascular wave is captured.

The blood pressure value derived by the correlation function with the time delay can be further adjusted based on various factors, such as an age, a gender, a height, a weight, an ethnicity, a BMI, an arm span, a health history, a health condition, a waist circumference, and an arterial distance between two physiological points of the person's body.

In a preferred embodiment, the blood pressure value of the person derived from the time delay can be provided to a user. The user can be the person whose blood pressure is measured. However, it is also contemplated that the user can be a third party, including a healthcare provider, a family member, an insurance provider, a personal trainer, or any other person or entities who are authorized to receive the person's health information.

In some embodiments, the user may receive the value of the cardiovascular time delay or one or more other metrics derived from the cardiovascular time delay. The metrics includes a life expectancy, a cardiovascular health, and an arterial compliance, arterial elasticity, or distensibility, which are positively correlated with the cardiovascular time delay. The metric may also include an arterial stiffness, a cardiovascular risk, a risk of morbidity, or a risk of mortality, which are negatively correlated with the cardiovascular time delay.

Followings are various examples and embodiments to measure blood pressures using one or more types of sensors in one or more mobile, wearable, or patch devices. It should be noted that any combinations of devices or sensors are contemplated in the present invention, and the present invention is not limited to the examples provided below.

EXAMPLES

Example 1: Measuring Blood Pressures Using a Microphone and a Photodetector (PCG+PPG)

The mobile computational device is comprised of an embedded electrical system, power source, and product housing. The embedded electrical system is comprised of, but not limited to, an electrical hardware circuit consisting of a digital controller, analog-to-digital converters, a software uploaded to the digital controller responsible for driving the hardware components to accomplish the defined tasks (e.g., sensor functionality, sensor signal capture, etc.), at least one acoustic-to-electrical converter (e.g., microphones), and at least one photodetector or image sensor component. The photodetector or image sensor component may include, but is not limited to, a semiconductor charge-coupled devices (CCD), an active pixel sensors in complementary metal-oxide-semiconductor (CMOS), or a N-type metal-oxide-semiconductor (NMOS, Live MOS) technologies. Herein either a photodetector or image sensor will be referred to as a photodetector.

FIG. 4A shows a perspective view of the product housing for the mobile computational device 400. FIG. 4B shows a side view of the product housing for the mobile computational device 410. The product housing consists of an acoustic duct 420 and one or more embedded acoustic-to-electrical converter components 425. At least one of the embedded acoustic-to-electrical converter components 425 are exposed to ambient air via opening 405 of the acoustic duct 420 for proper capture of incident acoustic waves.

FIG. 4C shows a schematic view of measuring acoustic heart activity 430 on the person's chest 450. To capture an acoustic heart acoustic wave 460 transmitted from the heart 440, the user is specifically instructed to place the opening 405 of the acoustic duct 420 of the mobile computational device product housing 400 in direct skin contact with his or her chest 450. To achieve improved capture of acoustical heart activity signals and improved blood pressure measurement accuracy, the user is further instructed to ensure that at least 50%, at least 70%, at least 90% or the entire perimeter surface of the opening 405 of the acoustic duct 420 of the product housing remains in constant contact with the skin of his or her chest 450. This instruction ensures a "skin-acoustic duct seal" that enables a confined column of air within the acoustic duct 420 to better propagate acoustical waves 460 generated by the person's heart 440 inside the chest cavity and results in improved conduction of such acoustical heart activity by the acoustic-to-electrical transducer of the mobile computational device embedded system.

At the same time the user is instructed to hold the acoustic duct of the mobile computational device product housing in direct, sealed contact with the person's chest, the user is also instructed to simultaneously place the palmar tissue bed of one of his or her hand digits/phalanx of the left or right arm in direct contact with the photodetector housing of the same mobile computational device. This position that the user must hold during a blood pressure measurement, which will be referred as the measurement position, is held for the duration of the blood pressure measurement.

Every cardiac cycle of the person's heart produces analog, physiological biosignals that include acoustic heart activity, arterial pressure wave activity, and local skin tissue blood volume activity. The human heart is a four chamber heart comprising two ventricles and two atria with two atrioventricular and two semilunar valves. Each atrioventricular valve facilitates the passage of blood from one atrium into one ventricle. Each semilunar valve facilitates the passage of blood from one ventricle into either the aorta or pulmonary artery. Within a single cardiac cycle blood fills each of the two atria, is then passed through each atrioventricular valve into each respective ventricle, then passed through each semilunar valve into the aorta (from the left ventricle) and the pulmonary artery (from the right ventricle). The blood that is ejected from the left ventricle of the heart into the aorta is then passed into either the left or right subclavian artery which feeds into the brachial artery of that arm which subsequently feeds into the radial and ulnar arteries which both feed the palmar digital arteries of the hand digits of the respective arm. The blood within the palmar digital arteries of each hand passes into the small microvasculature of the subcutaneous and dermal tissue within the palmar tissue bed of each digit.

The acoustic heart activity trace captured in this method contains physiological information about the occurrence of the closure of the atrioventricular and semilunar valves of the person's heart as well as physiological information about the timing related to the ejection of blood from the left ventricle of the heart into the aorta and peripheral arterial tree. During each cardiac cycle, the closure of both the atrioventricular and semilunar valves produce acoustic signals (acoustic heart activity). Specifically, the near-synchronous closure of both atrioventricular valves produce one predominant acoustic wave at one point in time (S1 acoustic wave) and the near-synchronous closure of both semilunar values produce a second predominant acoustic wave at a later point in time (S2 acoustic wave). The acoustic heart activity is comprised of, but not limited to, the S1 and S2 acoustic waves. The turbulent closure of heart valves causes acoustic perturbations that can be detected with a proper acoustic transducer (e.g., a stethoscope). Signal peak detection and common bandpass signal processing techniques are used to isolate the frequencies of interest in the acoustic heart activity trace signal, particularly, but not limited to, those below 1000 Hz, and used to identify the precise time reference associated with the following information: left ventricular contraction/blood ejection from the heart into the aorta for a single cardiac cycle, left ventricular ejection time (LVET), pre-ejection period (PEP), the opening and closing of the atrioventricular and semilunar valves.

During each cardiac cycle, blood that is ejected from the left ventricle into the aorta produces an incident arterial blood pressure wave that propagates through the subclavian artery through the arterial artery through the radial and ulnar arteries through the palmar digital arteries of the hand and into the small microvasculature of the subcutaneous and dermal tissue within the palmar tissue bed of each digit of each hand. The propagating arterial pressure wave causes localized compression of and therefore localized increases to blood volume along its trajectory in the arterial tree. Human blood contains intrinsic biophysical properties in which it absorbs incident light photons. With each cardiac contraction an arterial pressure wave is generated and propagated along the arterial tree to the periphery of the cardiovascular system, reaching the microvasculature of the subcutaneous and dermal tissue of the skin. The propagating arterial pressure wave causes localized compression of and therefore localized increases to blood volume along its trajectory in the arterial system. Because larger volumes of blood absorb larger amounts of incident light photons, changes in subcutaneous and dermal tissue blood volume are detectable with the proper use of a photodetector aimed at or in direct contact with the subcutaneous and dermal tissue bed.

In some embodiments, sampling of digitized outputs of the photodetector and acoustic-to-electrical transducer may be conducted in a different frequency, and the sensor data may be updated asynchronously. To synchronously obtain sensor data from two different sensors, the software running on the processor of the embedded system of the mobile computational device initiates a measurement session of which initiation is triggered by user interaction with the mobile computational device. The software allocates memory space within the embedded system either on a memory-equipped digital controller component or dedicated memory component to hold in memory slots for 1) the most recent digital value of the acoustic-to-electrical transducer, 2) the most recent digital value of the photodetector, and 3) the session signal trace buffer.

The software activates the acoustic-to-electrical transducer. Incident, analog acoustic waves of the acoustic heart activity induce fluctuations in outputted electrical activity of the acoustic-to-electrical transducer. This electrical output is digitized via a dedicated analog-to-digital converter component, an analog-to-digital converter equipped digital controller component, or any hardware component within the embedded electrical system equipped with the ability to convert an analog electrical signal into a discretely sampled digital signal. Updates of the digitized outputs of the acoustic-to-electrical transducer, of which each update will be referred herein as the latest acoustic digital value, are routed into and handled by the software where a specific thread or loop of code is responsible for receiving the latest acoustic digital values. The software activates the photodetector and an available incident light source (e.g., a camera flash). The incident light source either is also in direct contact with the palmar tissue bed of the same digit or nearby. Periodic cardiac contractions lead to localized increases to blood volume at the person's palmar tissue bed of the digit in contact with the photodetector. These localized increases to blood volume cause more light to be absorbed and less light to be reflected back to the photodetector. Incident, analog fluctuations in reflected light from the palmar tissue bed of the person's digit in contact with the photodetector induce either fluctuations in outputted electrical activity of the photodetector, which is subsequently digitized via a dedicated analog-to-digital converter component, an analog-to-digital converter equipped digital controller component, or any hardware component within the embedded electrical system equipped with an analog to digital converter, or fluctuations in the individual color components (e.g., RGB components) of pixels from an image sensor type photodetector. Updates of the digitized outputs of the photodetector, either in the form of frames comprised of pixels each pixel of which is comprised of a red, green, and blue component (for an image-type photodetector) or single-value intensity values. The latest photodetector digital values are routed into and handled by the software where a specific thread or loop of code is responsible for receiving the latest photodetector digital values.

Every time the latest acoustic digital value is routed into and handled by the software, it is stored in memory as the most recent digital value of the acoustic-to-electrical transducer. Every time the latest photodetector digital value is routed into and handled by the software, it is stored in memory as the most recent digital value of the photodetector.

In asynchronous periodic fashion, the software runs another thread or loop of code, which is responsible for grabbing the most recent digital value of the acoustic-to-electrical transducer stored in memory and the most recent digital value of the photodetector stored in memory. At the same time, the software generates a time stamp, as precise as possible, but ideally precise to one millisecond or less. The three values are appended to the session signal trace buffer in memory, generating a synchronized set of parallel physiological signal traces.

The Local Tissue Blood Volume Activity trace captured in this method contains physiological information about the pulsatile fluctuations of blood volume present in the microvasculature and capillary beds of a region of tissue on the surface of the body. The physiological information, represented as a plethysmogram, can be shown in a waveform. In the waveform, detection of a signal foot, a maximal slope, or a peak of the waveform can be used to identify the precise time reference associated with the arrival of an arterial pressure wave generated from a single cardiac cycle/left ventricular contraction of the heart.

Once the precise time references associated with the left ventricular contraction of the heart and arterial pressure wave arrival at the local tissue region (e.g., the palmar tissue bed of the person's hand phalanx) are captured, the time delay associated with the subsequent arrival of the arterial pressure wave after the left ventricular contraction of the heart (the Pulse Transit Time A) is calculated by mathematical operation of subtraction between the two time references.

Once the Pulse Transit Time A is captured, a systolic blood pressure can be measured based on a linear relationship between Pulse Transit Time A and systolic blood pressure as a function of p=Mt+N, where p is a systolic blood pressure, t is a pulse transit time A (PTT_A) and M and N are coefficients.

Once the Pulse Transit Time A is captured, a diastolic blood pressure can be measured based on a linear relationship between Pulse Transit Time A and diastolic blood pressure as a function of p=Mt+N, where p is a diastolic blood pressure, t is a pulse transit time A (PTT_A) and M and N are coefficients.

Example II: Measuring Blood Pressures Using an Accelerometer and a Photodetector (BCG+PPG)

Figure 5A:
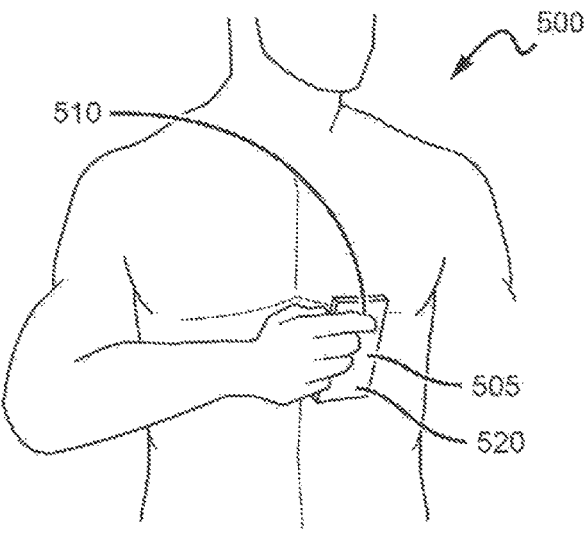
FIGS. 5A-B illustrate one exemplary embodiment of blood pressure measurement by using a mobile computational device to record a ballistocardiogram and a plethysmogram.

FIG. 5A shows an example of a method and system to measure blood pressures using raw digital signal traces related to the mechanical heart activity of the person 500, represented as BCG signals, and local tissue blood volume activity, represented as PPG signals. In a preferred embodiment, both signals can be captured by a single mobile computational device 505 equipped with an accelerometer and a photodetector.

The mobile computational device 505 can be placed anywhere on the chest, preferably near the apex of the heart as a point of contact 520. It is contemplated that any orientation of the mobile computational device sufficiently coupled to the chest can capture the mechanical heart activity from the accelerometer sensor. Orientations can include, but is not limited to, pressing a side of the device 505 to the chest, pressing the screen of the device to the chest, or pressing the back of the device 505 to the chest with sufficient physical coupling to capture the mechanical heart activity. The person whose blood pressure is measured can be oriented in any position, including a sitting position, standing, or supine position. However, it is preferred that the vertical distance (measured along the gravitational force axis) between the person's location of PPG measurement 510 (e.g., a finger) and the fixed location of the heart is zero during the duration of the measurement to ensure the hydrostatic influences are minimized.

Figure 11A:
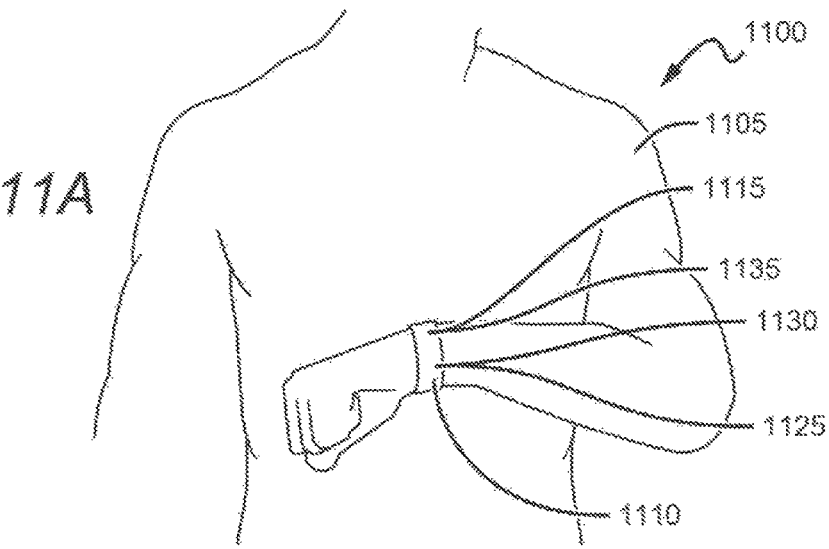
FIGS. 11A-B illustrate one exemplary embodiment of blood pressure measurement by using a wearable device to record a plethysmogram and a ballistocardiogram.

In other embodiments, raw digital signal traces related to the mechanical heart activity of the person and local tissue blood volume activity of a person can be captured by a single wearable computational device, which is equipped with an accelerometer 1135 and a photodetector. FIG. 11A shows a schematic view 1100 of a person 1105 measuring the blood pressure using a wearable device 1130. In this method and system, the person 1105 wears a wearable computational device 1130 on the left or right arm, the wrist, forearm, or upper arm. The wearable device 1130 is equipped with an accelerometer and one or more photoemitter and one or more photodetector components collectively forming a PPG Sensor 1110. The PPG Sensor 1110 is built into the product housing of the wearable device 1130. The PPG Sensor 1110 is in direct contact with the person's skin of the arm at a point of contact A 1125, and maintains constant contact with the skin. While still being worn on the arm of the person 1105, the wearable device 1130 is put into contact with the chest of the person at a point of contact B 1115. The wearable device 1130 can be placed anywhere on the chest of the person 1105, but with ideal placement near the apex of the heart. Any orientation of the wearable device sufficiently coupled to the chest to capture the mechanical heart activity from the accelerometer sensor is sufficient.

The person whose blood pressure is measured can be oriented in any positions, including a sitting position, standing position, or supine position. However, it is preferred that the vertical distance (measured along the gravitational force axis) between the person's location of PPG measurement 1125 (e.g., the wrist) and the fixed location of the heart is zero during the duration of the measurement to ensure the hydrostatic influences are minimized.

The physiological action of the heart of the person produces heart and local tissue displacement detected by the wearable device accelerometer 1135, which detects the real-time transient changes in the person's BCG signal. BCG signals provide information of the time, at which each heart contraction occurs and the force of each heart contraction. Simultaneously, the PPG Sensor 1110 measures the real-time transient changes in blood flow at the point of contact A 1125 that provide information of the time of each pulse arrival produced by each contraction of the person's heart.

Figure 5B:
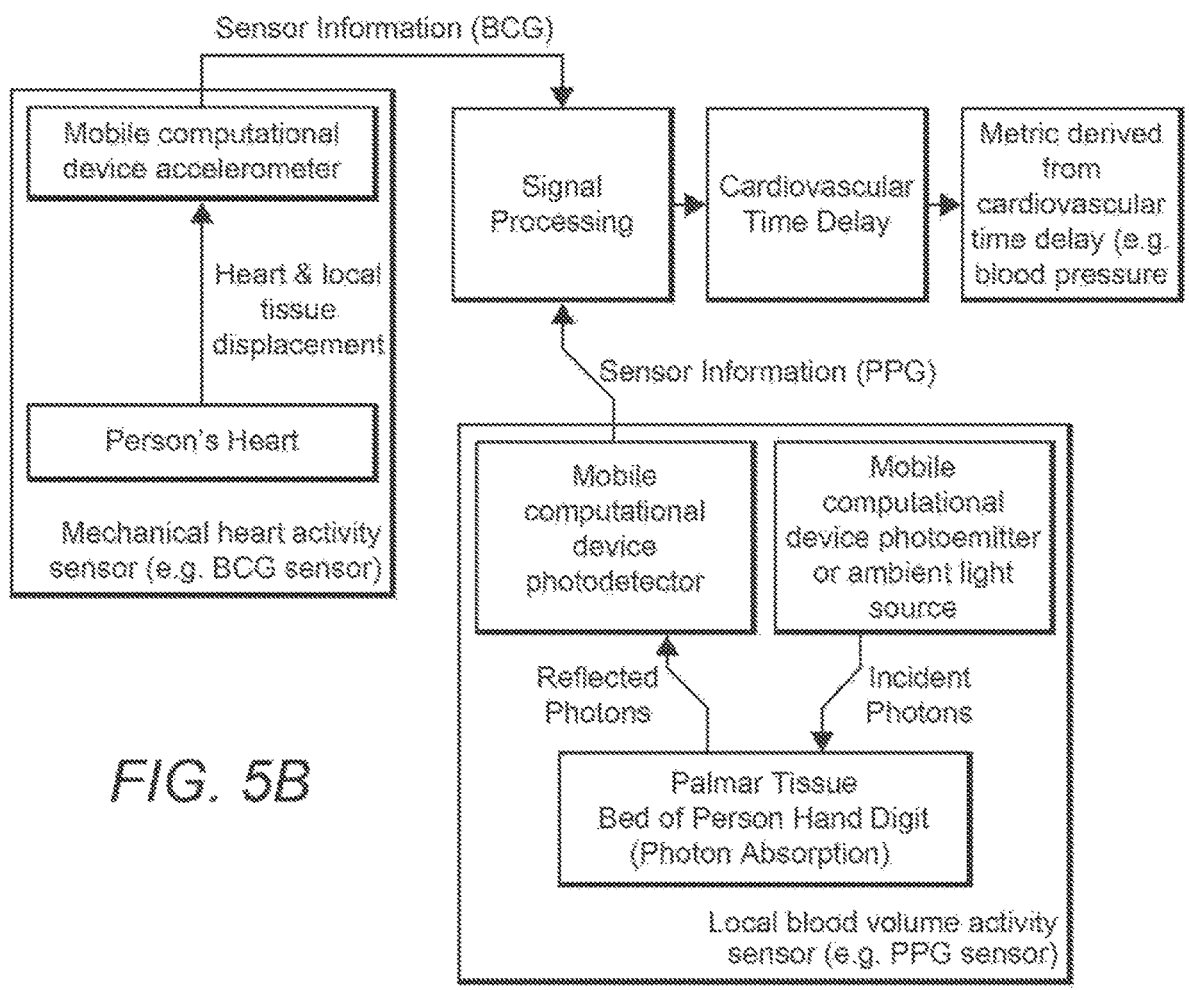
Figure 11B:
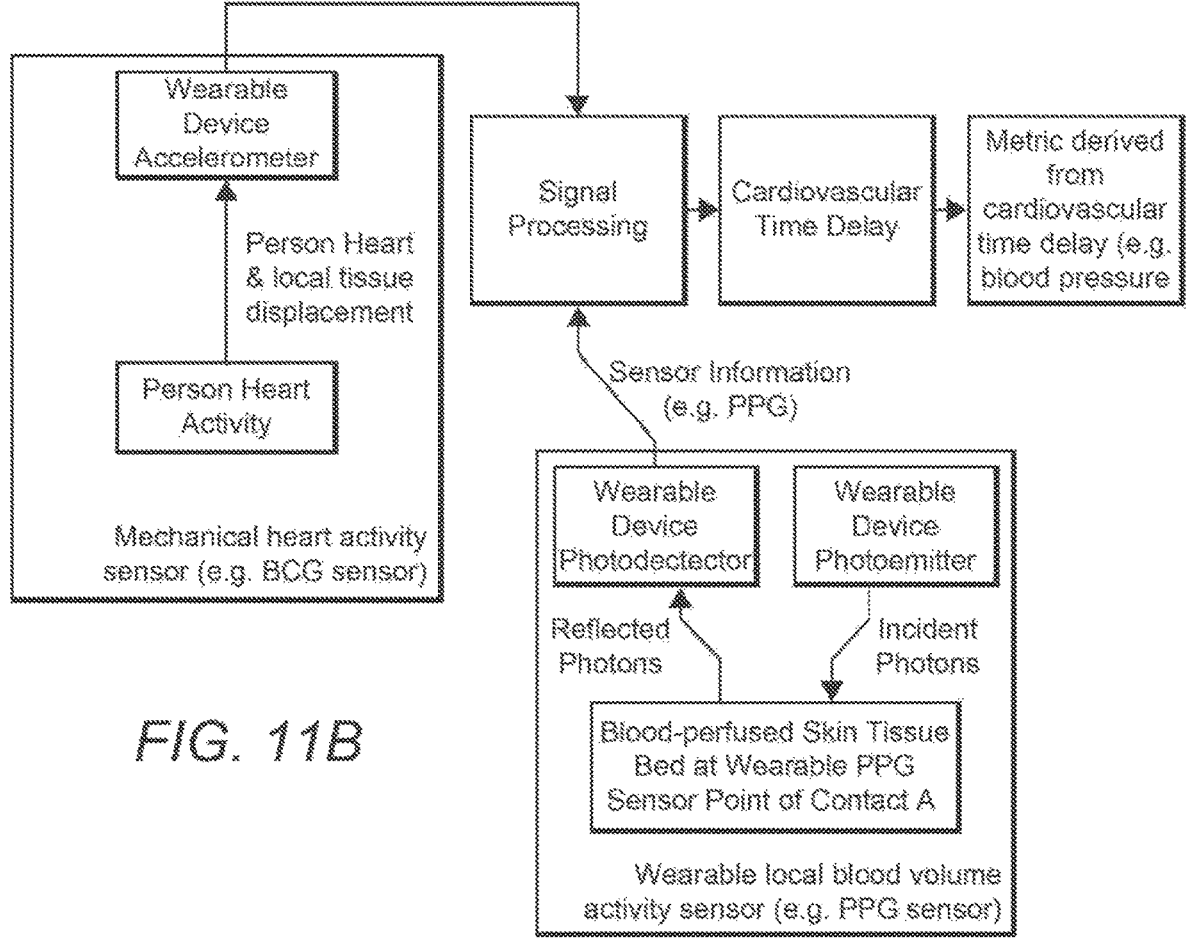

FIGS. 5B and 11B show schematic diagrams to process BCG signals and PPG signals in two different embodiments, respectively. The mechanical heart activity and the local tissue blood volume activity of a person are captured and data features (e.g., time reference) are derived from at least one or more data points as described above. Once the precise time reference associated with the mechanical systole or ventricular cardiac contraction event is selected as the time reference for the left ventricular contraction event/time of blood ejection from the heart and time reference associated with the arterial pressure wave arrival at the local tissue region (e.g., the palmar tissue bed of the person's hand phalanx) are both captured, the time delay associated with the subsequent arrival of the arterial pressure wave after the left ventricular contraction of the heart (the Pulse Transit Time B) is calculated by mathematical operation of subtraction between the two time references. The Pulse Transit Time B does not include the delay known as the Pre-Ejection Period, which is the time delay between electrical systolic of the ventricles of the heart and mechanical left ventricular contraction/blood ejection from the heart into the aorta. Because of this, using the Pulse Transit Time B can more accurately measure blood pressures.

Once the Pulse Transit Time B is captured, a systolic blood pressure can be measured based on a linear relationship between Pulse Transit Time B and systolic blood pressure as a function of p=Mt+N, where p is a systolic blood pressure, t is a pulse transit time B (PTT_B) and M and N are coefficients.

Once the Pulse Transit Time B is captured, a diastolic blood pressure can be measured based on a linear relationship between Pulse Transit Time B and diastolic blood pressure as a function of p=Mt+N, where p is a diastolic blood pressure, t is a pulse transit time B (PTT_B) and M and N are coefficients.

Example III: Measuring Blood Pressures Using an Accelerometer and a Microphone (BCG+PCG)

The combination of using an accelerometer and a microphone to detect BCG signal and PCG signal, respectively, would provide more information about the cardiac cycle. Capturing PCG signals using a microphone provides information of the total time period in which blood is ejecting from the left ventricle during each cardiac cycle and information of the total time period in which blood is not ejecting from the left ventricle during each cardiac cycle. However, PCG signals may not provide the precise moment in time, in which blood ejection from the left ventricle into the aorta begins, but an approximation of it from the time of S1. PCG signals do provide the precise moment in time in which blood ejection from the left ventricle into the aorta ends (beginning of the S2 component of closure of the aortic semilunar valve). BCG signals captured by the accelerometer can provide information of the moment of maximum ventricular contraction, which is associated with a point in time within the time period of blood ejection from the left ventricle into the aorta. Therefore, combination of PCG data with BCG data can provide a new approximate parameter that aids with a more accurate blood pressure calculation. Such new parameters include the time period between 1) the beginning of blood ejection from the left ventricle into the aorta, 2) the time of maximum blood ejection from the left ventricle into the aorta, which is the time that corresponds with maximum mechanical activity detected by the BCG and 3) the ending of blood ejection from the left ventricle into the aorta.

Example IV: Measuring Blood Pressures Using at Least Two Photodetectors (PPG+PPG)

Figure 6A:
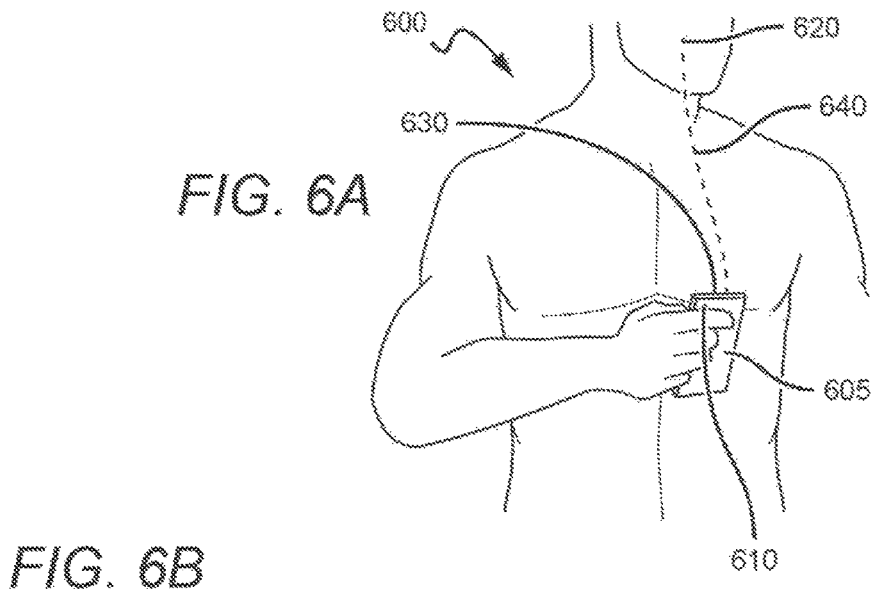
FIGS. 6A-B illustrate one exemplary embodiment of blood pressure measurement by using a mobile computational device to record two plethysmograms.

FIG. 6A shows an example of a method and system to measure blood pressures using raw digital signal traces related to the local tissue blood volume activity, represented as PPG signals of the person 600. In this method and system, a single mobile computational device 605 equipped with at least two photodetectors 610, 630 is used to capture PPG signals at least in two different parts of the person's body.

The user is instructed to aim a first photodetector (e.g., a camera lens of a mobile computational device 605) at, but not limited to the location of the person's face. Ambient incident photons interact with the blood-perfused skin tissue bed of the person at his or her face and are reflected along a path 640 and captured by the first photodetector 630 of mobile computational device 605. The time of arrival of a cardiovascular pulse wave at the face produced by each contraction of the person's heart is detected. Concurrently, the user is instructed to cover a second photodetector 610 and the device's flash LED with the person's hand digit/phalanx palmar tissue bed region. The second photodetector detects the time of the arrival of a cardiovascular pulse wave at the person's digit/phalanx palmar tissue bed region produced by each contraction of the person's heart.

In a preferred embodiment, the first location for capturing the local tissue blood volume activity of the person is preferably located at a different cardiovascular distance from the heart than the second location for capturing the local tissue blood volume activity of the person. For example, the first location of capturing local tissue blood volume activity with a first photodetector 630 may be a portion of the face 620 of the person (e.g., the forehead, the cheeks under the eyes, the entire face, the chin, etc.). The skin tissue bed of the person's wrist, arm, or finger can be used as the second location of contact with the second photodetector 610 of the mobile device 605 to capture the local tissue blood volume activity. However, it is contemplated that other parts of the body can be used as a second location of contact.

Figure 7A:
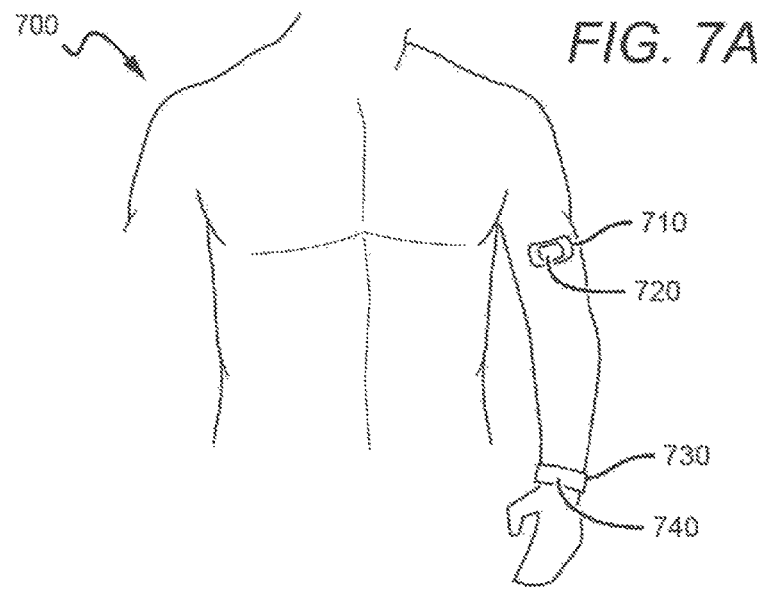
FIGS. 7A-B illustrate one exemplary embodiment of blood pressure measurement by using a patch and a wearable device to record two plethysmograms at different locations of the body.

In other embodiments, raw digital signal traces related to the local tissue blood volume activity of a person can be captured by one or more wearable devices to continuously measure blood pressure as the person goes about their day without the need for the user to stop what they are doing to take a measurement. In this method and system shown in FIG. 7A, at least two computational wireless devices 720, 730 are used to capture the local tissue blood volume activity. Each of wireless devices is a wearable device with one or more photodetectors 710, 740.

The first photodetector 710 contacts the skin tissue bed of the person's wrist, arm, or finger as the location of contact for the wearable device responsible for capturing the local tissue blood volume activity. However, other part of the body can be used such as the person's foot (e.g., with a wearable sock with embedded sensor). The second photodetector 740 contacts the skin of the portion of the person's body, which has different distance from the heart from the first sensor capturing the local tissue blood volume activity. In a preferred embodiment, these two wearable devices could both be patches. However, it is also contemplated that one device is a patch and the other device is another type of wearable devices (e.g. a fitness tracker, a wristband, a smart watch, etc.).

Figure 6B:
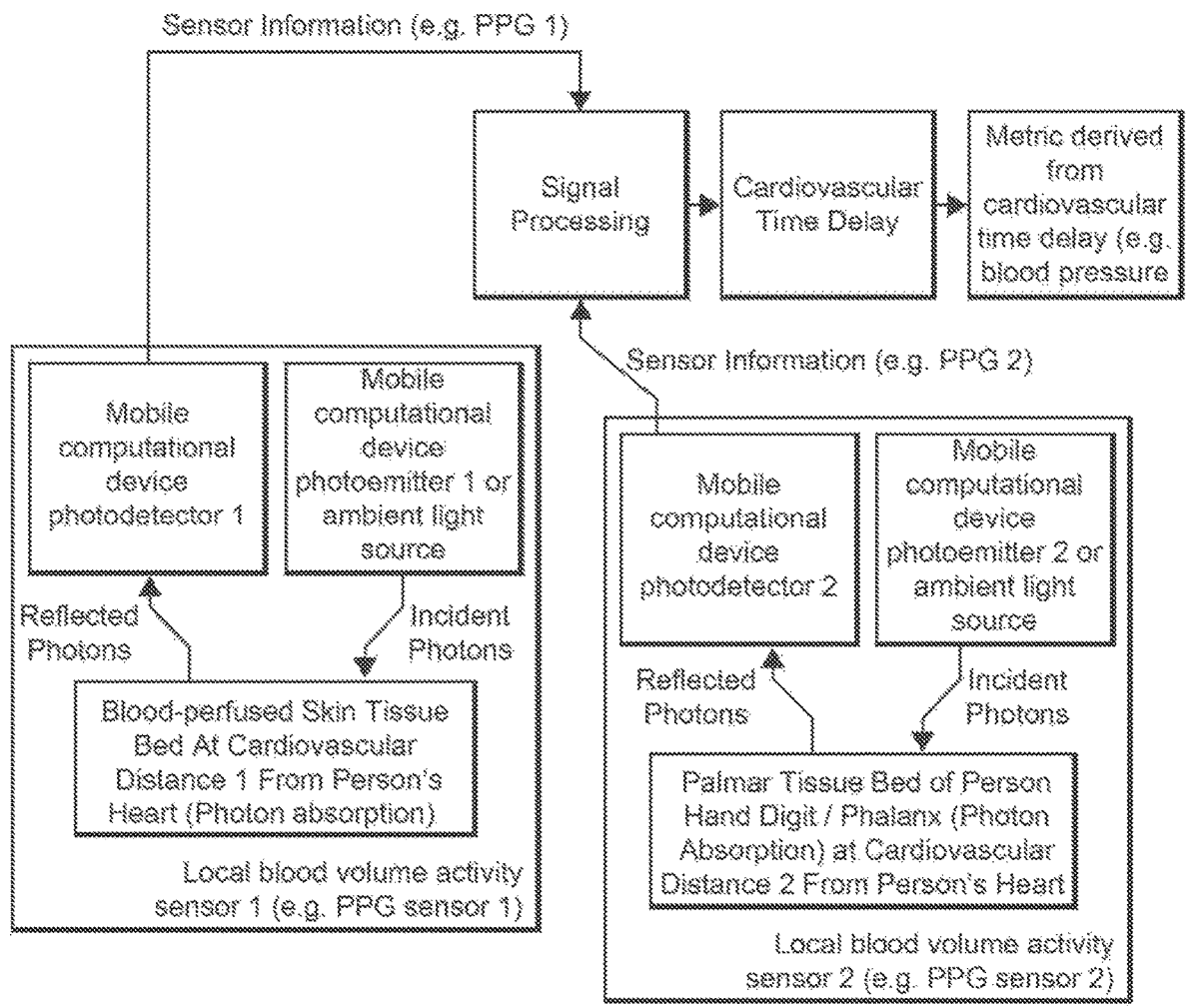
Figure 7B:
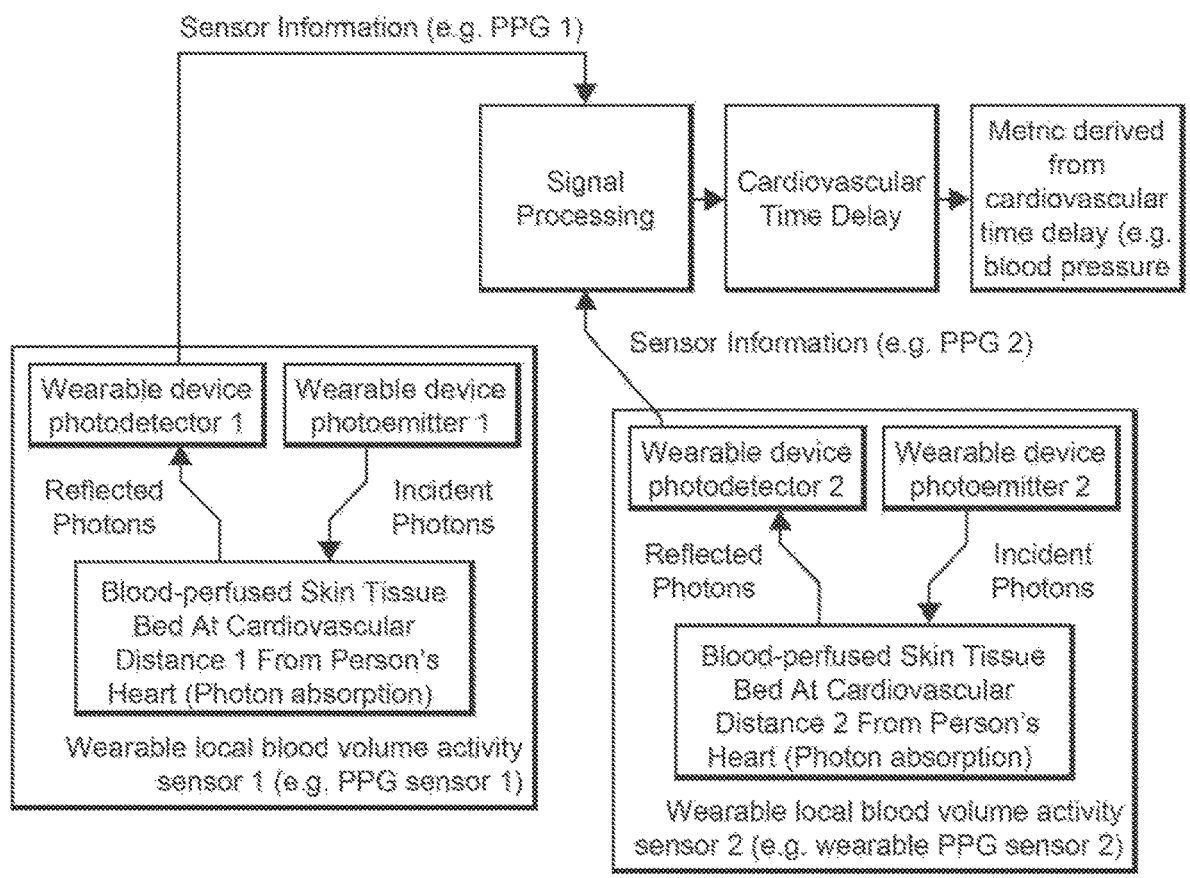

FIGS. 6B and 7B show schematic diagrams to process two PPG signals in two different embodiments, respectively. The signals for local tissue blood volume activity of a person are captured and data features (e.g., time reference) are derived from at least one or more data points as described above. Once the precise, first time reference associated with the first arterial pressure wave arrival at the local tissue region of interest of the first sensor (e.g., tissue bed of the person's hand, finger, arm, leg, torso) and the second time reference associated with the first arterial pressure wave arrival at the local tissue region of interest of the second sensor (e.g., the tissue bed of the person's face) are both captured, the time delay associated with the subsequent arrival of the arterial pressure wave (the Pulse Transit Time C) is calculated by mathematical operation of subtraction between the two time references.

Once the Pulse Transit Time C is captured, a systolic blood pressure can be measured based on a linear relationship between Pulse Transit Time C and systolic blood pressure as a function of p=Mt+N, where p is a systolic blood pressure, t is a pulse transit time C (PTT_C) and M and N are coefficients.

Once the Pulse Transit Time C is captured, a diastolic blood pressure can be measured based on a linear relationship between Pulse Transit Time C and diastolic blood pressure as a function of p=Mt+N, where p is a diastolic blood pressure, t is a pulse transit time C (PTT_C) and M and N are coefficients.

Example V: Measuring Blood Pressures Using an Array of Electrodes and a Photodetector (ECG+PPG)

FIG. 8A-B shows an example of a method and system to measure blood pressures using raw digital signal traces related to the electrical heart activity of the person 800, represented as ECG signals, and local tissue blood volume activity, represented as PPG signals. In a preferred embodiment, both signals can be captured by one mobile device 810 with a photodetector 805 as shown in FIG. 8A, and a wearable device 820 with an array of electrode 830 as shown in FIG. 8B. It is contemplated that both devices are configured to facilitate wireless communication. The data flow of the two devices is facilitated in the following fashion; the wearable device communicates electrical heart activity signal trace data via wireless communication to the mobile computational device with the photodetector, where the two signals are synchronized in time. Wireless communication may be carried out via, but by no means limited to, short-range electromagnetic radio frequency communication using the frequency band of 2.4 GHz, in which case both devices are equipped with 2.4 GHz electromagnetic radios. An alternative means of wireless communication that could be employed involves the wearable device with the electrode array being equipped with an electrical-to-acoustic transducer (e.g., a speaker) capable of producing inaudible high-frequency sounds whose instantaneous sound frequency emissions vary in direct proportion to the instantaneous values of the electrical heart activity. Such inaudible sounds are detected by an acoustic-to-electrical transducer (e.g., a microphone) on the mobile computational device with the photodetector.

In the method and system shown in FIG. 8, the wearable electrical heart sensor is placed on the chest or back for proper trans-thoracic capture of the electrical activity of the heart, which are locations capable of providing an adequately strong signal to noise ratio for the capture of the electrical heart activity trace of the person. However, it is also contemplated that the wearable device can be placed on the lower body, including the abdomen or lower back, or the upper portion of the body, including the neck or behind the ear.

Figure 9A:
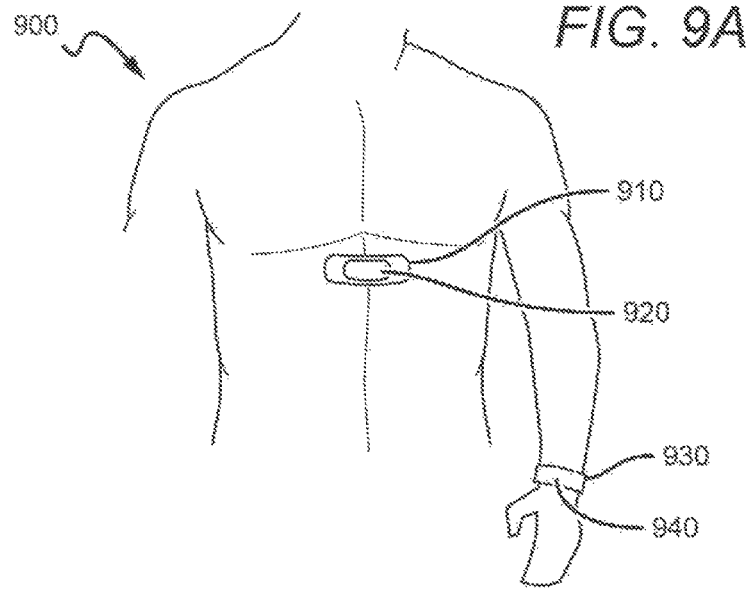
FIGS. 9A-B illustrate one exemplary embodiment of blood pressure measurement by using a patch and a wearable device to record an electrocardiogram and a plethysmogram.
Figure 9B:
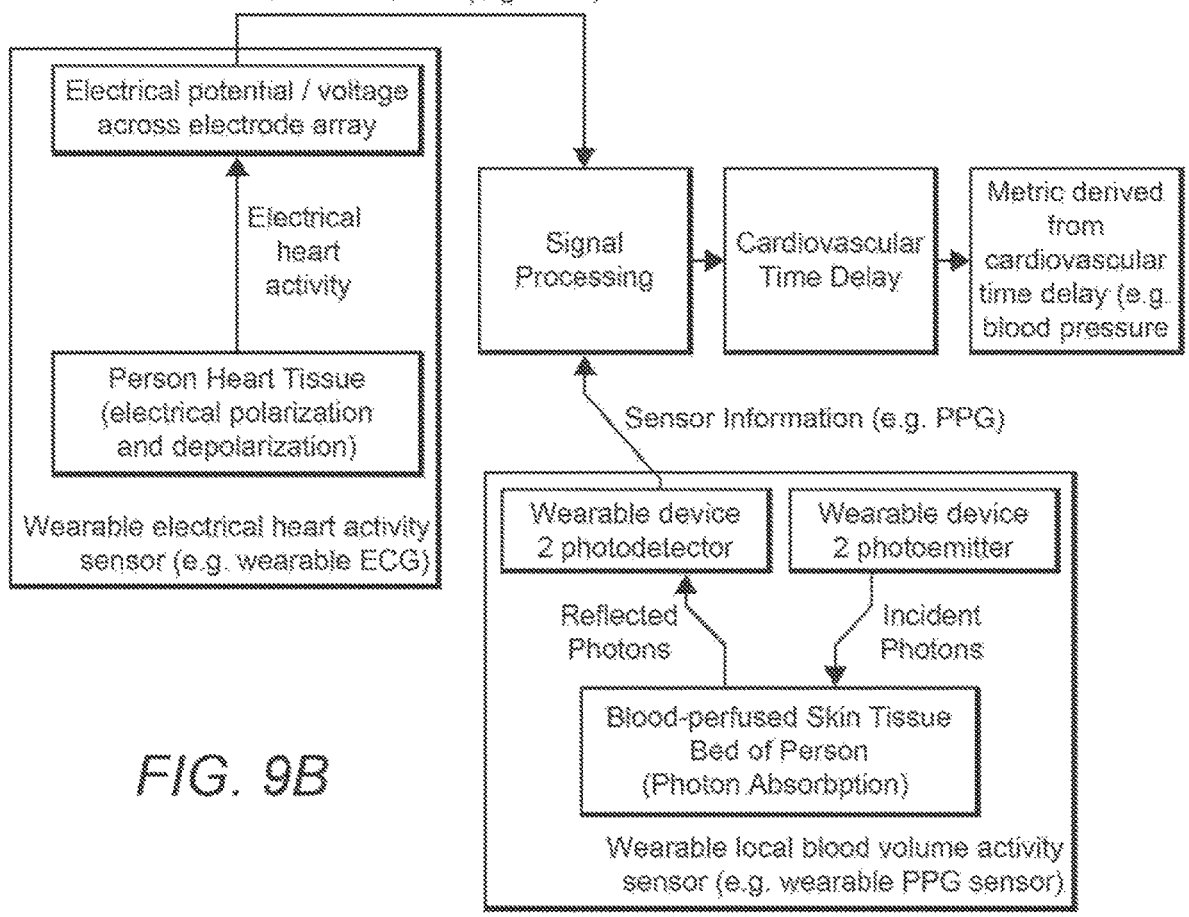

In other embodiment, as shown in FIG. 9A, ECG signals and PPG signals can be captured by two wearable devices 910, 930 to continuously measure blood pressure as the person 900 goes about their day without the need for the user to stop what they are doing to take a measurement. In this method and system shown in FIG. 9, the first wearable device 910 has an array of electrode 920, which can capture ECG signals from the person's heart activity. The second wearable device 930 contacts the skin tissue bed of the person's wrist, arm, or finger as the location of contact for the wearable device responsible for capturing the local tissue blood volume activity. However, other part of the body can be used such as the person's foot (e.g., with a wearable sock with an embedded sensor). The first wearable device 910 can be placed on the chest or back of the person 900 for proper transthoracic capture of the electrical activity of the heart. However, it is also contemplated that the wearable device 910 can be placed on the lower body, including the abdomen or lower back, or the upper portion of the body, including the neck or behind the ear.

Figure 10A:
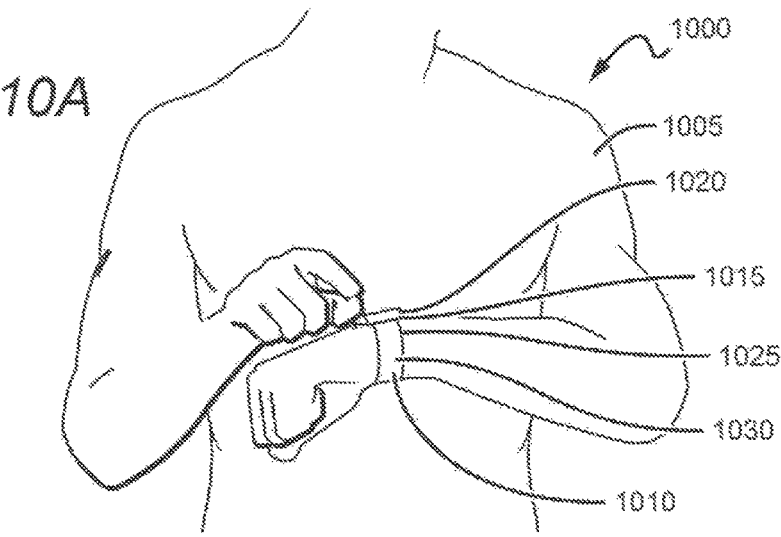
FIGS. 10A-B illustrate one exemplary embodiment of blood pressure measurement by using a wearable device to record an electrocardiogram and a plethysmogram.
Figure 10B:
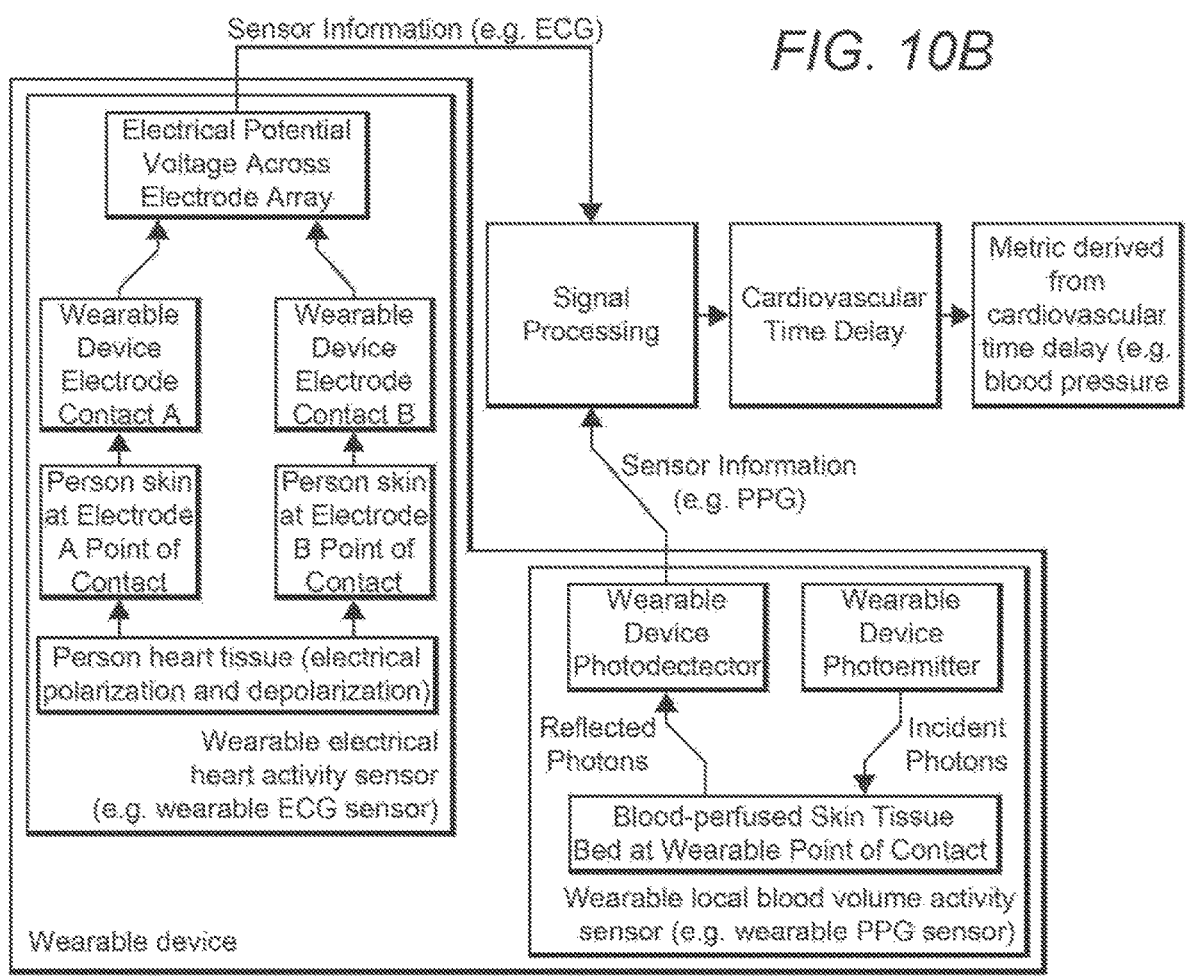

In some other embodiments, as shown in FIG. 10A, only one wearable device 1010 can be used to capture both ECG and PPG signals from the person's heart activity. In this method and system, the device is equipped with an electrode array with an array of at least two electrodes (ECG sensor) and a photodetector (PPG sensor). In this method and system, ECG sensors 1030 may contact the skin tissue bed of the person's wrist, arm, or finger 1005, 1020, 1025. The ECG sensors 1030 may also contact the skin of the chest or back of the person 1000. However, it is also contemplated that the wearable device can be placed on the lower body, including the abdomen or lower back, or the upper portion of the body, including the neck or behind the ear. The PPG sensors 1015 may contact the skin tissue bed of the person's wrist, arm, or finger 1005, 1020, 1025. However, other part of the body can be used such as the person's foot (e.g., with a wearable sock with embedded sensor).

Figure 12A:
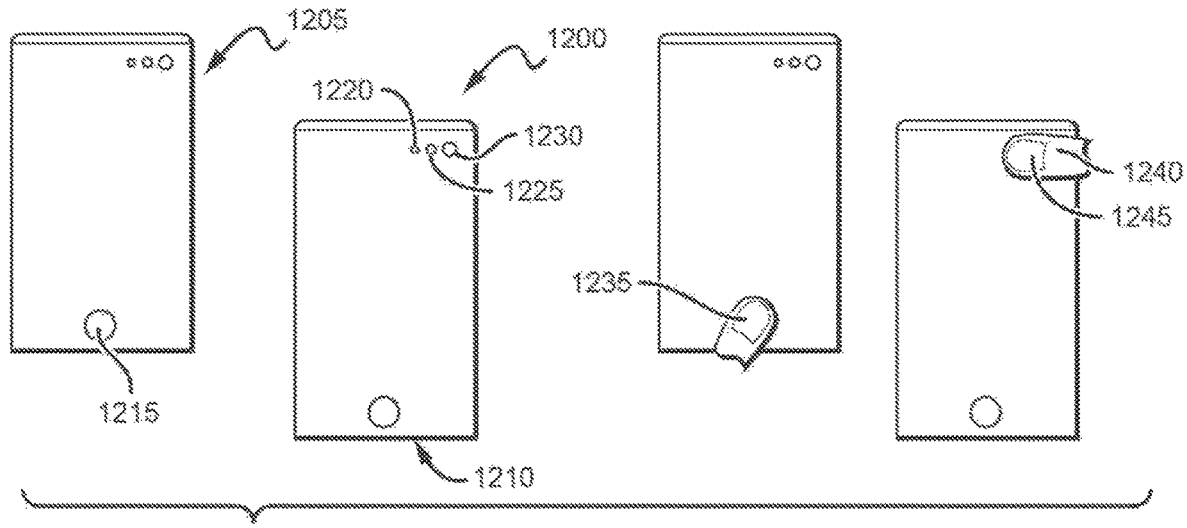
FIGS. 12A-B illustrate one exemplary embodiment of blood pressure measurement by using a mobile computational device to record an electrocardiogram and a plethysmogram.
Figure 12B:
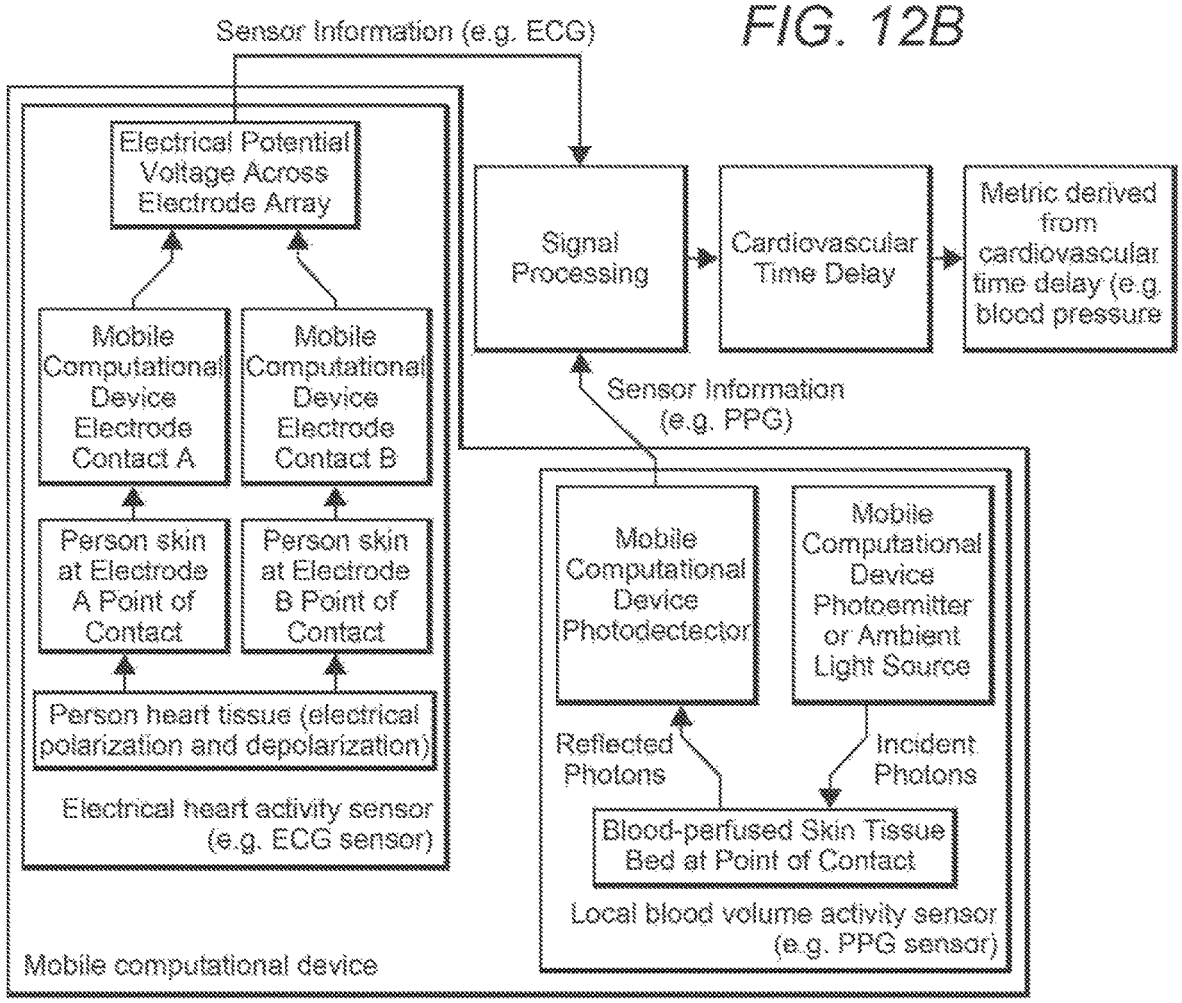

In some other embodiments, as shown in FIG. 12A, only one mobile device 1200 may be used to capture both ECG and PPG signals from the person's heart activity, in this method and system, the device 1200 is equipped with an electrode array with an array of at least two electrode contacts (ECG sensor) 1215, 1220. The device 1200 is also equipped with one or more photoemitters 1225 and one or more photodetector components 1230, which may include, but is not limited to, a Camera flash LED and Camera lens, collectively forming a PPG Sensor. The front view 1205 of the mobile device 1200 shows a first electrode 1215. The rear view 1210 of the mobile device 1200 shows a photodetector 1230, photoemitter 1225 and a second electrode contact 1220.

In this method and system, two electrode contacts 1215, 1220 are capable of measuring an electrical potential drop across the two electrode contacts 1215, 1220 through their interconnected circuitry. The user is instructed to place the skin of one hand 1235 in direct contact with electrode contact A 1215 and the skin of the opposing hand 1240 in direct contact with electrode contact B 1220 forming the "ECG Sensor. The user is also instructed to place the hand digit/phalanx palmar tissue bed region 1 of one of the hands over the PPG Sensor components. The real-time transient changes in electrical potential across electrode contact A and electrode contact B form a continuous quantification of the electrical activity of the person's heart (ECG signals) and among other heart-based physiological parameters, the ECG signal is used to detect the time at which each heart contraction occurs. Simultaneously, the PPG Sensor measures the real-time transient changes in blood flow at the point of contact 1245 of the opposing hand 1240. Together, the person's ECG and the person's PPG enable the derivation of a cardiovascular time delay, which is used to produce a measure of blood pressure.

FIGS. 8C, 9B, 10B, and 12B show schematic diagrams to process ECG signal and PPG signal in three different embodiments, respectively. The signals for a person's heart's electrical activity and local tissue blood volume activity of the person are captured, and data features (e.g., time reference) are derived from at least one or more data points as described above. Once the precise time reference associated with the electrical systole (and subsequent left ventricular contraction of the heart) and time reference associated with the arterial pressure wave arrival at the local tissue region of interest (e.g., the palmar tissue bed of the person's hand digit/phalanx) are both captured, the time delay associated with the subsequent arrival of the arterial pressure wave after the electrical systolic (the Pulse Arrival Time) is calculated by mathematical operation of subtraction between the two time references. The Pulse Arrival Time includes a delay known as the Pre-Ejection Period, which is the time delay between electrical systolic of the ventricles of the heart and mechanical left ventricular contraction/blood ejection from the heart into the aorta.

Once the Pulse Arrival Time is captured, a systolic blood pressure can be measured based on a linear relationship between Pulse Arrival Time and systolic blood pressure as a function of p=Mt+N, where p is a systolic blood pressure, t is a pulse arrival time (PAT) and M and N are coefficients.

Once the Pulse Arrival Time is captured, a diastolic blood pressure can be measured based on a linear relationship between Pulse Arrival Time and diastolic blood pressure as a function of p=Mt+N, where p is a diastolic blood pressure, t is a pulse arrival time (PT) and M and N are coefficients.

Example VI: Measuring Blood Pressures Using an Array of Electrodes and an Accelerometer (ECG+BCG)

There is a time delay between the time of peak electrical depolarization of the ventricles and the time of peak, mechanical contraction of the ventricles referred to as the Pre-Ejection Period (PEP). The combination of BCG signal and ECG signal provides information of an indication of the pre-ejection period between electrical systole and mechanical systole of the heart. Furthermore, it provides an easy way to capture PEP (time between peak electrical depolarization of the ventricles and peak mechanical contraction of the ventricles), which correlates with contraction force of the heart. Contraction force of the heart correlates with systolic blood pressure (as systolic blood pressure is a pressure that results both from arterial vascular activity as well as heart/ventricular activity). Thus, this PEP value can be used as an additional piece of information to improve the accuracy of blood pressure measurement calculations.

Example VII: Measuring Blood Pressures Using Three Types of Sensor Information: A Combination of Three of the Following: ECG, EEG, PPG, PCG, and IPG In some embodiments, at least three types of sensors or sensor information may be used together to derive blood pressure of the person. Three types of sensors may be placed in one mobile or wearable device. It is also contemplated that two sensors are placed in one mobile or wearable device, and the other sensor is placed in another mobile or wearable device. It is also contemplated that three types of sensors are placed in three distinct mobile or wearable devices.

In these embodiments, a software configured to obtain a first sensor information from a first sensor, a second sensor information from a second sensor, and a third sensor information from a third sensor near simultaneously. The first sensor information comprises a first data point, the second sensor information comprises a second data point, and the third sensor information comprises a third data point. Based on the first, second, and third data points, first data feature, second data feature, and the third data feature can be derived, respectively.

As described above, ECG is used to capture a time reference, which is mostly by measuring the time associated with the R-peak, related to the electrical systole/depolarization event of a single cardiac cycle. BCG is used to capture a time reference relating to the positive or negative maximum slopes, a peak, or a foot of the BCG waveform related to the mechanical systole event of a single cardiac cycle. PPG is used to capture a time reference relating to the a foot, a maximum slope, or a peak of an incident PPG waveform related to the arrival of an arterial pulse pressure wave at a tissue region of interest some arterial distance away from the heart. IPG is used to capture a time reference relating to a foot, a maximum slope, or a peak of an incident IPG waveform related to the arrival of an arterial pulse pressure wave at a tissue region of interest some arterial distance away from the heart. PCG is used to capture a time reference relating to the mechanical systole event of a single cardiac cycle by detecting the S heart sound.

Combination of ECG, BCG, and PPG

Pre-ejection period (PEP) is a time delay between electrical systole and mechanical systole of the heart. Use of ECG-PPG dual sensor methods to capture a cardiovascular time delay may introduce errors in such a time delay because it includes the PEP, which varies independent of blood pressure along the arterial tree. By employing three sensors, ECG, BCG, PPG to derive the value of blood pressure, accuracy in blood pressure measurement can be improved because the BCG sensor information and derived time reference associated with mechanical systole of the heart can be used to identify the PEP for each cardiac cycle of the heart.

Combination of ECG, BCG, and IPG

Pre-ejection period (PEP) is a time delay between electrical systole and mechanical systole of the heart. Use of ECG-IPG dual sensor methods to capture a cardiovascular time delay may introduce errors in such a time delay because it includes the PEP, which varies independent of blood pressure along the arterial tree. By employing three sensors, ECG, BCG, and IPG to derive blood pressure, accuracy in blood pressure measurement can be improved because the BCG sensor information and derived time reference associated with mechanical systole of the heart can be used to identify the PEP for each cardiac cycle of the heart.

Combination of ECG, PCG, and PPG

S1 event in PCG corresponds to the mechanical systole of the heart. Hence, the PCG is used to identify in this method the mechanical systole of the heart by capturing the S sound. Pre-ejection period (PEP) is a time delay between electrical systole and mechanical systole of the heart. Use of ECG-PPG dual sensor methods alone to capture a cardiovascular time delay that correlates to blood pressure can be subject to a rather significant error. This potential error is caused by the PEP, which is included in the cardiovascular time delay. By adding a PCG sensor to two sensors, ECG and PPG, to measure blood pressure, accuracy in blood pressure measurement can be improved because the PCG sensor information and derived time reference associated with mechanical systole of the heart can be used to identify and eliminate the PEP for each cardiac cycle of the heart from the cardiovascular time delay used to measure blood pressure.

Combination of ECG, PCG, and IPG

S1 event in PCG corresponds to the mechanical systole of the heart. Hence, the PCG is used to identify in this method the mechanical systole of the heart by capturing the S1 sound. Pre-ejection period (PEP) is a time delay between electrical systole and mechanical systole of the heart. Use of ECG-PPG dual sensor methods alone to capture a cardiovascular time delay that correlates to blood pressure can be subject to a rather significant error. This potential error is caused by the PEP, which is included in the cardiovascular time delay. By adding a PCG sensor to two sensors, ECG and IPG, method of measuring blood pressure, accuracy in blood pressure measurement can be improved because the PCG sensor information and derived time reference associated with mechanical systole of the heart can be used to identify and eliminate the PEP for each cardiac cycle of the heart from the cardiovascular time delay used to measure blood pressure.

Combination of BCG, PCG, and PPG

In this method, PCG is used to capture the left ventricular ejection time (LVET) by identifying the delay between a time reference within the S1 heart sound and a time reference within the S2 heart sound of the same cardiac cycle. Thus, PCG can be used to improve the accuracy of the systolic blood pressure measurement because LVET is captured in addition to the cardiovascular time delay already captured that correlates with both systolic and diastolic blood pressure that is calculated by a delay associated with a point in the BCG wave and a point within the PPG wave. The value of LVET is used to adjust the coefficients in the relationship that is used to derive BP from PIT (e.g., in a linear fashion: the M and N coefficients in a function of $p=Mt+N$).

Sensor information of ECG, BCG, PPG, PCG or IPG can be obtained and data features from each sensor information on each data point are derived as described above. Once data features are derived, one or more time delays are derived based on the correlation among the three data features. In a preferred embodiment, the time delay is derived from a cross-correlation between the first data feature and the second data feature. For example, a first time delay can be derived based on the first data feature and the second data feature, a second time delay based on the first data feature and the third data feature, and a third time delay based on the second data feature and the third data feature.

The time delay derived based on three time references is correlated with the blood pressure value. In some embodiments, it is contemplated that the blood pressure value and the time delay can be linearly correlated as a function of $P=Mt+N$, where P is a systolic or diastolic blood pressure, M and N are coefficients, t is a time delay (e.g., pulse transit time). In other embodiments, it is contemplated that the blood pressure value and the time delay can be non-linearly correlated as a function of $P=Me^{-Nt}$, where P is a systolic or diastolic blood pressure, M and N are coefficients, t is a time delay (e.g., pulse transit time). In some other embodiments, it is also contemplated that the blood pressure value and the time delay can be sigmoidally correlated. It is preferred that at least two of three time delays are correlated to a blood pressure value of the person. However, it is also contemplated that only one of three time delays is correlated to a blood pressure value of the person.

The blood pressure value derived by the correlation function with the time delay can be further adjusted based on various factors, such as an age, a gender, a height, a weight, an ethnicity, a BMI, an arm span, a health history, a health condition, a waist circumference, and an arterial distance between two physiological points of the person's body.

The derived blood pressure value can be provided to a user. The user can be the person whose blood pressure is measured. However, it is also contemplated that the user can be a third party, including a healthcare provider, a family member, an insurance provider, a personal trainer, or any other person or entities who are authorized to receive person's health information.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. A method of measuring blood pressure of a person, comprising:
obtaining a plurality of waveforms from a device comprising:
an accelerometer;
a microphone; and
a photodetector;
wherein the plurality of waveforms comprises:
a first waveform captured using the accelerometer using at least one axis of acceleration from the accelerometer, where the at least one axis of acceleration is selected based on the position of the device relative to a coronal plane of the person;
a second waveform captured using the photodetector near a skin of the person; and
a third waveform captured using the microphone; and
where the first waveform, second waveform, and third waveform are captured near simultaneously;
deriving, using a set of one or more processors communicatively coupled to the device, a first data feature based on the first waveform, a second data feature based on the second waveform, and a third data feature based on the third waveform;
deriving, using the set of one or more processors, two time delays based on the first data feature, the second data feature, and the third data feature, where each of the two time delays is derived based on two of: the first data feature, the second data feature, and the third data feature;
deriving, using the set of one or more processors, a blood pressure measurement of the person based on the two time delays; and
providing to a user the blood pressure measurement of the person.

2. The method of claim 1, wherein the first data feature comprises one of the following: a peak of the first waveform, a foot of the first waveform, a point of maximum slope of the first waveform, a point of minimum slope of the first waveform, a time to peak of the first waveform, a width of a peak of the first waveform, a peak of the first or second derivative of the first waveform, a foot of the first or second derivative of the first waveform, a point of maximum slope of the first or second derivative of the first waveform, and a point of minimum slope of the first or second derivative of the first waveform.

3. The method of claim 1, wherein the first waveform is obtained near the heart of the person using only one of the axes of acceleration from the accelerometer.

4. The method of claim 1, further comprising the step of synchronizing the first waveform and the second waveform with a time stamp.

5. The method of claim 1, wherein the device is a wearable device.

6. The method of claim 1, wherein the device is a smart phone.

7. The method of claim 1, wherein one of the two time delays is derived from a cross-correlation between the first data feature and the second data feature.

8. The method of claim 1, further comprising adjusting the blood pressure measurement based on at least one of the following: an age, a gender, a height, a weight, an ethnicity, a BMI, an arm span, a health history, a health condition, a waist circumference, and an arterial distance between two physiological points of the person's body using the set of one or more processors.

9. The method of claim 1, wherein the skin is at a finger of the person.

10. The method of claim 1, wherein the skin is at a wrist of the person.

11. A blood pressure monitoring system for measuring blood pressure of a person, comprising:

a device comprising:
  an accelerometer;
  a photodetector; and
  a microphone;
  where the device is configured to:
    capture a first waveform using the accelerometer using at least one axis of acceleration from the accelerometer, where the at least one axis of acceleration is selected based on the position of the device relative to a coronal plane of the person;
    capture a second waveform using the photodetector near a skin of the person; and
    capture a third waveform using the microphone; and
    where the first waveform, second waveform, and third waveform are captured near simultaneously;
  a set of one or more processors; and
  a memory containing software capable of directing the set of one or more processors to:
    derive a first data feature based on the first waveform, a second data feature based on the second waveform, and a third data feature based on the third waveform;
    derive two time delays based on the first data feature, the second data feature, and the third data feature, where each of the two time delays is derived based on two of: the first data feature, the second data feature, and the third data feature;
    derive a blood pressure measurement of the person based on the two time delays; and
    provide to a user the blood pressure measurement of the person.

12. The system of claim 11, wherein the first data feature comprises one of the following: a peak of the first waveform, a foot of the first waveform, a point of maximum slope of the first waveform, a point of minimum slope of the first waveform, a time to peak of the first waveform, a width of a peak of the first waveform, a peak of the first or second derivative of the first waveform, a foot of the first or second derivative of the first waveform, a point of maximum slope of the first or second derivative of the first waveform, and a point of minimum slope of the first or second derivative of the first waveform.

13. The system of claim 11, wherein the first waveform is obtained near the heart of the person using only one of the axes of acceleration from the accelerometer.

14. The system of claim 11, wherein the software is further capable of directing the set of one or more processors to synchronize the first waveform and the second waveform with a time stamp.

15. The system of claim 11, wherein the device is a wearable device.

16. The system of claim 11, wherein the device is a smart phone.

17. The system of claim 11, wherein the software is further capable of directing the set of one or more processors to derive one of the two time delays from a cross-correlation between the first data feature and the second data feature.

18. The system of claim 11, wherein the software is further capable of directing the set of one or more processors to adjust the blood pressure measurement based on at least one of the following: an age, a gender, a height, a weight, an ethnicity, a BMI, an arm span, a health history, a health condition, a waist circumference, and an arterial distance between two physiological points of the person's body.

19. The system of claim 11, wherein the device further comprises the set of one or more processors and the memory.

20. A method of measuring a cardiovascular time delay of a person, comprising:
  obtaining a plurality of waveforms from a device comprising:
    an accelerometer;
    a microphone; and
    a photodetector;
  where the plurality of waveforms comprises:
    a first waveform captured using the accelerometer using at least one axis of acceleration from the accelerometer, where the at least one axis of acceleration is selected based on the position of the device relative to a coronal plane of the person;
    a second waveform captured using the photodetector near a skin tissue bed of the person; and
    a third waveform captured using the microphone;
    where the first waveform, second waveform, and third waveform are captured near simultaneously;
  deriving, using a set of one or more processors communicatively coupled to the device, a first data feature based on the first waveform, a second data feature based on the second waveform, and a third data feature based on the third waveform;
  deriving, using the set of one or more of processors, a cardiovascular time delay and a second time delay based on the first data feature, the second data feature, and the third data feature, where the cardiovascular time delay and the second time delay are each derived based on two of: the first data feature, the second data feature, and the third data feature;
  adjusting, using the set of one or more processors, the cardiovascular time delay based on the second time delay; and
  providing to a user at least one of the adjusted cardiovascular time delay value and a metric derived from the adjusted cardiovascular time delay of the person.

21. The method of claim 20, wherein the first data feature comprises one of the following: a peak of the first waveform, a foot of the first waveform, a point of maximum slope of the first waveform, a point of minimum slope of the first waveform, a time to peak of the first waveform, a width of a peak of the first waveform, a peak of the first or second derivative of the first waveform, a foot of the first or second derivative of the first waveform, a point of maximum slope of the first or second derivative of the first waveform, and a point of minimum slope of the first or second derivative of the first waveform.

22. The method of claim 20, wherein the first waveform is obtained near the heart of the person using only one of the axes of acceleration from the accelerometer.

23. The method of claim 20, further comprising the step of synchronizing the first waveform and the second waveform with a time stamp.

24. The method of claim 20, wherein the device is a wearable device.

25. The method of claim 20, wherein the device is a smart phone.

26. The method of claim 20, wherein one of the two time delays is derived from a cross-correlation between the first data feature and the second data feature.

27. The method of claim 20, wherein the skin tissue bed is at a finger of the person.

28. The method of claim 20, wherein the skin bed is at a wrist of the person.

* * * * *